(12) United States Patent
Yokoyama et al.

(10) Patent No.: US 7,381,415 B2
(45) Date of Patent: *Jun. 3, 2008

(54) COMPOSITE POWDER AND COSMETIC CONTAINING THE SAME

(75) Inventors: Hiroyuki Yokoyama, Yokohama (JP);
Satoshi Tomomasa, Yokohama (JP);
Kenichi Sakuma, Yokohama (JP);
Norinobu Yoshikawa, Yokohama (JP);
Eriko Kawai, Yokohama (JP);
Shigeyuki Ogawa, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 64 days.

This patent is subject to a terminal disclaimer.

(21) Appl. No.: 10/509,660

(22) PCT Filed: Mar. 28, 2003

(86) PCT No.: PCT/JP03/03946

§ 371 (c)(1),
(2), (4) Date: Sep. 29, 2004

(87) PCT Pub. No.: WO03/082229

PCT Pub. Date: Oct. 9, 2003

(65) Prior Publication Data

US 2005/0181067 A1    Aug. 18, 2005

(30) Foreign Application Priority Data

Mar. 29, 2002 (JP) ............................. 2002-096254
Mar. 29, 2002 (JP) ............................. 2002-096255
Dec. 6, 2002 (JP) ............................. 2002-355789
Dec. 6, 2002 (JP) ............................. 2002-355790

(51) Int. Cl.
*A61K 8/02* (2006.01)

(52) U.S. Cl. ............................................ 424/401

(58) Field of Classification Search ............... 424/401, 424/489, 490
See application file for complete search history.

(56) References Cited

U.S. PATENT DOCUMENTS 5,482,720 A * 1/1996 Murphy et al. ............ 424/489

FOREIGN PATENT DOCUMENTS

EP    1112744 A1    7/2001
FR    2729132 A1    7/1996

* cited by examiner

*Primary Examiner*—San-ming Hui
(74) *Attorney, Agent, or Firm*—Fei-Fei Chao; Andrews Kurth, LLP

(57) ABSTRACT

A first subject of the present invention is a composite powder having antibacterial and antifungal effect, in which a base powder, zinc oxide and/or zinc basic carbonate, and alkali metal salt are combined.

In the composite powder, it is preferable that the base powder is an adsorbing site for adsorbing a specified enzyme, and a site in which zinc oxide and/or zinc basic carbonate and alkali metal salt are combined is an acting site having enzyme inhibiting or activating property.

In the composite powder, it is preferable that the zeta-potential of an adsorbing site at pH to be used is a negative value, and the zeta-potential of an adsorbing site at pH 7.5 is −10 mV or lower.

A second subject of the present invention is a cosmetic composition comprising the aforementioned composite powder.

The composite powder can be also used as a skin roughening improving agent, a sensitive skin caring agent or a pimpled skin caring agent.

17 Claims, 6 Drawing Sheets

COMPOSITE POWDER AND COSMETIC CONTAINING THE SAME

RELATED APPLICATIONS

This application claims priority to the Japanese Patent Application Nos.2002-96254 filed on Mar. 29, 2002 and 2002-96255 filed on Mar. 29, 2002 and 2002-355790 filed on Dec. 6, 2002 and 2002-355789 filed on Dec. 6, 2002 is hereby incorporated with reference for all purposes.

BACKGROUND OF THE INVENTION

1. Field of the Invention

This invention relates to composite powder and cosmetic composition containing the same, in particular, their improvement of the antibacterial and antifungal activity, and also relates to a composite powder having both of plasminogen activator (PA) inhibitory activity and antibacterial and antifungal activity and a cosmetic containing the same.

2. Prior Art

Many kinds of antibacterial and antifungal agents are used in extremely wide area in the human life (food, clothing and shelter). These agents are typically divided into organic group and inorganic group.

Organic antibacterial and antifungal agents include paraben, triclosan, quaternary ammonium salt, chlorhexidine hydrochloride, thiabendazole, carbenedazine, captan, fluorofolpet, chlorothalonil and so on.

On the other hand, inorganic antibacterial and antifungal agents mainly include silicate, phosphate, zeolite, synthetic mineral and so on, retaining or substituting with antibacterial metals such as in particular silver, copper, and zinc. Among them, for example, silver- or zinc-substituted zeolite, silver-retaining apatite, silver-retaining silica gel and so on are put to practical use.

These antibacterial and antifungal agents could prevent products from bacterial or fungal infection, contamination, and deterioration by using them in the preparation of construction materials, daily necessities and so on. However, it rarely happened that these antibacterial and antifungal agents possess stimulation on human bodies.

On the other hand, not only morbid dermatitis such as atopic dermatitis and severe pimpled skin, but also so-called sensitive skin exhibiting hypersensitive response to environmental change although it is not morbid, are problematic and, when an antibacterial and antifungal agent is used in a composition which is directly applied to a human body such as cosmetic compositions, safe and mildly stimulative antibacterial and antifungal agent is demanded.

Since the organic antibacterial and antifungal agents such as paraben and the like which are commonly used as preservatives of cosmetic compositions have possibility to show skin stimulative action, it have been desired to develop excellent inorganic antibacterial and antifungal agents.

Conventional inorganic antibacterial and antifungal agents, compared with organic ones, are safe for human body and are hard to be influenced by heat, chemical agents, and so on. However these inorganic agents generally show rather low antifungal activity. Accordingly the development of inorganic agents possessing excellent antibacterial and antifungal activities has been desired.

SUMMARY OF THE INVENTION

The present invention was done in view of the aforementioned previous problems, and an object thereof is to provide a composite powder having excellent antibacterial and antifungal activity besides plasminogen activator inhibitory activity, and a cosmetic containing the same.

In view of the aforementioned problems, the present inventors intensively studied and found out that a composite powder containing zinc oxide and/or zinc basic carbonate and alkali metal salt has excellent antiseptic effect even when an small amount of an organic composite powder such as paraben or none of the powder is used. Further, the present inventors found out that excellent PA inhibiting effect is exerted, in addition to antibacterial and antifungal activity by combining an acting site comprising zinc oxide and/or zinc basic carbonate and alkali metal salt with an adsorbing site which adsorbs a specified enzyme.

That is, a first subject of the present invention is a composite powder having antibacterial and antifungal effect, in which a base powder, zinc oxide and/or zinc basic carbonate, and alkali metal salt are combined.

In the composite powder, it is preferable that the base powder is an adsorbing site for adsorbing a specified enzyme, and a site, in which zinc oxide and/or zinc basic carbonate and alkali metal salt are combined, is an acting site having enzyme inhibiting or activating property.

It is preferable that the composite powder is in a form in which surface of the base powder is covered with zinc oxide and/or zinc basic carbonate and alkali metal salt in stripe or spot state;

in a form in which a surface of the base powder is covered with zinc oxide and/or zinc basic carbonate and alkali metal salt in net state;

in a form in which zinc oxide and/or zinc basic carbonate and alkali metal salt are encapsulated, embedded or included in the base powder.

In addition, in the composite powder, it is preferable that an acting site and an adsorbing site are formed on an inactive powder in stripe or spot state.

In the composite powder, it is preferable that alkali metal salt is encapsulated, embedded or included in zinc oxide and/or zinc basic carbonate.

In the composite powder, it is preferable that the specified enzyme is plasminogen activator, and the acting site is a site having plasminogen activator inhibitory property.

In the composite powder, it is preferable that the alkali metal salt is 1 or more than 2 selected from the group consisting of hydroxide, hydrogen carbonate and carbonate of lithium, sodium and potassium.

In the composite powder, it is preferable that the zeta-potential of an adsorbing site is a negative value at used pH, and the zeta-potential of an adsorbing site at pH 7.5 is −10 mV or lower.

In the composite powder, it is preferable that the adsorbing site is 1 or more than 2 selected from the group consisting of silica, talc, mica, polyamide, polymethyl methacrylate or silicone resin.

In the composite powder, it is preferable that a content of alkali metal salt is 0.5 to 50% by weight relative to the whole powder, and a content of zinc oxide and/or zinc basic carbonate is 5 to 75% by weight relative to the whole powder.

In the composite powder, it is preferable that, as a raw material for synthesizing zinc oxide and/or zinc basic carbonate, zinc acetate, zinc chloride or zinc sulfate containing acetic acid at the same time is used.

In the composite powder, it is preferable that an inhibiting rate of plasminogen activator is 40% or larger.

An inhibiting rate of plasminogen activator (PA) is measured by the following method: An inhibiting rate of urokinase (UK) that is a kind of PA is measured.

Assessment is performed by measurement of activity of a buffer containing 0.1% of a test sample and double-stranded UK-type PA (30 U/mL). The activity means degradation activity of both samples to synthetic substrate.

It is preferable that pH of 10% by weight of the composite powder dispersion in water is 9 to 14.

It is preferable that the composite powder is obtained by continuously supplying an aqueous solution containing zinc ion and an alkali aqueous solution to a reactor containing a base powder while amounts of the two aqueous solutions to be added dropwise are adjusted so that pH of the reaction solution is retained constant between 7 to 10 under room temperature and atmospheric pressure, and filtering the product, followed by washing with water and drying.

A second subject of the present invention is a cosmetic composition comprising the aforementioned composite powder.

It is preferable that the cosmetic composition does not substantially contain other antibacterial and antifungal agent.

The composite powder can be also used as a skin roughening improving agent, a sensitive skin caring agent or a pimpled skin caring agent.

DESCRIPTION OF THE PREFERRED EMBODIMENT

Figure 1:
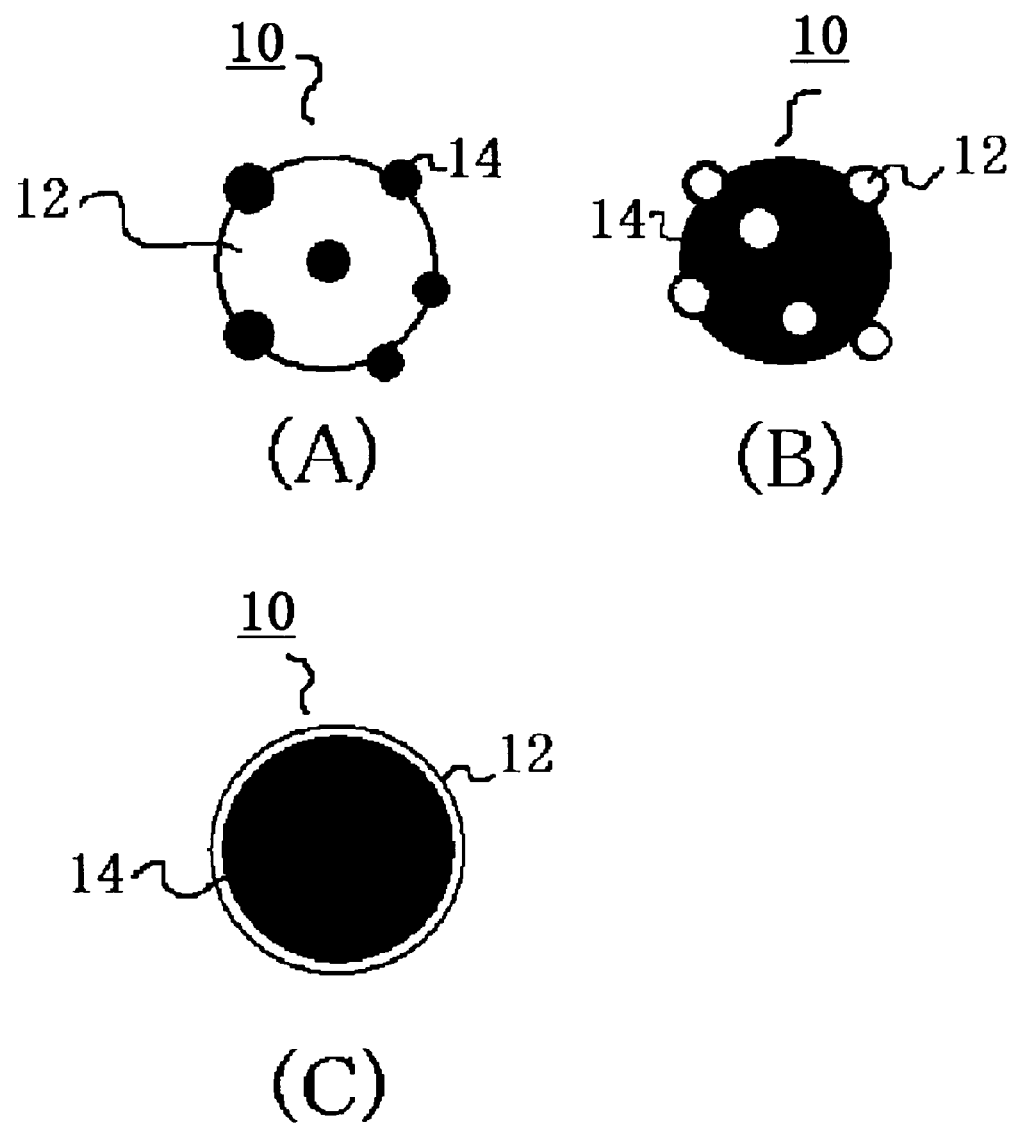
FIG. 1 is a view showing an example of the structure of the composite powder according to this invention.

Preferable embodiments of the present invention will be explained below.

The composite powder of the present invention is such that a base powder, zinc oxide and/or zinc basic carbonate, and alkali metal salt are combined.

As the combined state, the state where a surface of a base powder is covered in stripe or spot state with zinc oxide and/or zinc basic carbonate, and alkali metal salt;
the state where a surface of a base powder is covered in net state with zinc oxide and/or zinc basic carbonate, and alkali metal salt 14;
and the state where zinc oxide and/or zinc basic carbonate, and alkali metal salt are encapsulated, embedded or included in a base powder ; are preferable. However, the state is not limited to them as far as the effect of the present invention is not deteriorated. Further, it is preferable that alkali metal salt is encapsulated, embedded or included in zinc oxide and/or zinc basic carbonate.

Zinc Oxide and/or Zinc Basic Carbonate

A synthesizing method of zinc oxide and/or zinc basic carbonate in the composite powder of the present invention is roughly classified into a wet method in which synthesis is performed in an aqueous solution, and a dry method in which a solution does not directly intervene. In the wet method, zinc basic carbonate can be generally obtained by mixing an aqueous solution containing a zinc ion and an alkali aqueous solution containing a carbonate ion, and washing the product with water, followed by filtration and drying. This can be further fired to obtain zinc oxide.

In addition, in the wet method, when a strong alkali aqueous solution such as sodium hydroxide and potassium hydroxide is used in place of an alkali aqueous solution containing a carbonate ion, this can be washed with water, and filtered and dried to obtain zinc oxide, since zinc oxide is directly synthesized not via zinc basic carbonate.

On the other hand, as the dry method, there are methods of heating metal zinc in the air (French method) and methods of heating Franklinite with a reducing agent such as a coal and a coke (American method), or the like.

Alkali Metal Salt

The composite powder of the present invention contains alkali metal salt. Specifically, it is preferable that the composite powder contains 1 or more than 2 alkali metal salt(s) selected from hydroxide, hydrogen carbonate and carbonate of lithium, sodium and potassium. In addition, it is preferable that the alkali metal salt is sodium carbonate or potassium carbonate. The composite powder can contain 1 or more than 2 of the aforementioned alkali metal salt(s).

Base Powder

Since the zinc oxide and/or zinc basic carbonate is a fine particle, it becomes difficult to spread in the case of blending it in a cosmetic at a large amount. However, by combining with a base powder having better usability, this defect can be overcome.

As a base powder the following thing can be listed.

Inorganic Base Powder

As an inorganic base powder, kaolin group such as kaolinite, dickite, nacrite, haloidsite, antigorite, chrysotile and so on; smectite group such as pyrophyllite, montmorillonite, nontronite, saponite, hectorite, bentonite and so on; illite group such as sericite, muscovite, lithia mica, synthetic mica and so on; silicate such as beidellite, aluminum silicate magnesium and so on; calcium compound such as phosphoric acid 3 calcium, hydroxyapatite and so on; magnesium silicate group such as talc, serpentine and so on; single component powder such as silica, alumina and so on; hard capsule such as zeolite, silicone powders, glass powders, glass beads, titanium oxide-involving-silica, zinc oxide-involving-silica, iron oxide-involving-silica, cerium oxide-involving-silica, titanium oxide-involving-PMMA(polymethyl methacrylate), zinc oxide-involving-PMMA, cerium oxide-involving-PMMA and so on; pearl pigment such as titanated mica, titanium oxide-barium sulfate, titanium oxide-tantalum, bismuth oxychloride, bismuth oxychloride-mica and so on can be listed.

Organic Base Powder

As an organic base powder, nylon powder, polyethylene powders, Teflon™ powders, polypropylene powders, silk powders, vinyl acetate powders, methacrylate powders, poly acrylonitrile powders, polystyrene powders, cellulose powder, and so on are listed.

Inorganic Pigment Base Powder

As an inorganic pigment base powder, white pigment such as titanium oxide, zinc oxide, zirconium oxide, cerium oxide and these complex oxides, and iron oxide, hydration iron oxide, chromium oxide, chromium hydroxide, ultramarineblue, deep blue, oxidation cobalt and so on are listed.

Organic Pigment Base Powder

As an organic pigment base powder, organic pigment such as Lithol Rubine B, Lithol Rubine***, Lake Red CBA, Lithol Red, Deep Maroon, Helindone Pink CN, Permaton Red, Permanent Red F5R, Permanent Orange, Benzidine orange G, Orange II, Hanza Yellow and Phthalocyanine Blue; zirconium, barium or aluminum lake such as Erythrosine, Phloxine B, Acid Red, Fast Acid Magenta, Eosine YS, Eosine YSK, Violamine R, Oil Red XO, Orange II, Tartrazine, Sunset Yellow FCF, Uranine, Uranin K, Quinaline Yellow WS, Fast Green FCF and Brilliant Blue FCF and so on are listed.

In the composite powder of the present invention, when the base powder acts as an adsorbing site to adsorb a specified enzyme, when a site active at which zinc oxide and/or zinc basic carbonate and alkali metal salt are combined, is an active site having the property of inhibiting or activating the enzyme, excellent PA inhibiting effect in addition to antibacterial and antifungal activity is exerted.

It is considered that a protein degrading enzyme (protease) in the epidermis cell plays an important role in normal process of keratinizing a skin, and it has been revealed that particularly change of activity of fibrinogenolysis proteases such as plasmin and plasminogen activator has particularly deep relation to the formation of disease images of various skin diseases. Plasmin is a protease whose precursor plasminogen has been activated by PA, and plays an important role in inhibition of thrombus formation in blood coagulation system, but it is known that when plasmin is overproduced, a harmful peptide which destructs a tissue or a cell by its non-specific protein degrading action, or can be a cause for inflammation or anaphylaxis shock such as dilation of blood capillary, sthenia of blood vessel permeability, constriction of smooth muscle, and pain is produced, influencing adversely on a living body. In addition, it has been reported that urokinase (UK) which is one of PA has activity of exasperating cell proliferation.

Examples of skin disease in which change in activity of fibrinolysis protease is confirmed including psoriasis and pemphigus vulgaris which is representative of inflammatory abnormal keratosic disease. In psoriasis, strong PA activity is confirmed at a parakeratosis site of the affected epidermis (Hibino et el.: Blood and Vessel; 17(6), 1986) and, in pemphigus vulgaris, PA produced in large amount in epidermis cell converts extracellular plasminogen into plasmin, and this plasmin digests a substance binding cells, whereby, a tissue fluid is pooled among cells, and intraepidermal bulla is formed (Morioka S.: J.Invest. Dermatol;76, 1981). In addition, it has been reported that in a skin in which epidermal cell is abnormally proliferated by stimulation such as cleanser, etc., and skin roughening is caused, plasminogen which should be originally localized around epidermal basal layer is activated by PA, and is dispersed as active plasmin in whole epidermal layer (Kitamura et al: Journal of Cosmetic Technology;29(2), 1995). From the foregoing, it has been thought that, in order to improve or prevent various skin diseases or proliferating abnormality of an epidermal cell, it is important to control activity of PA. However, in the former antibacterial and antifungal agents, no agent having skin disease improving or preventing effect has been reported.

Structure of Composite Powder

In the composite powder 10 of the present invention, as typically shown in FIG. 1A, adsorbing site 12 is covered in stripe state or in spot state with an acting site 14.

In addition, as shown in FIG. 1B, the acting site 14 is covered in stripe state or in spot state with an adsorbing site 12. Alternatively, as shown in FIG. 1C, the adsorbing site 12 is formed on whole surface of an acting site 14 in net state.

Figure 2:
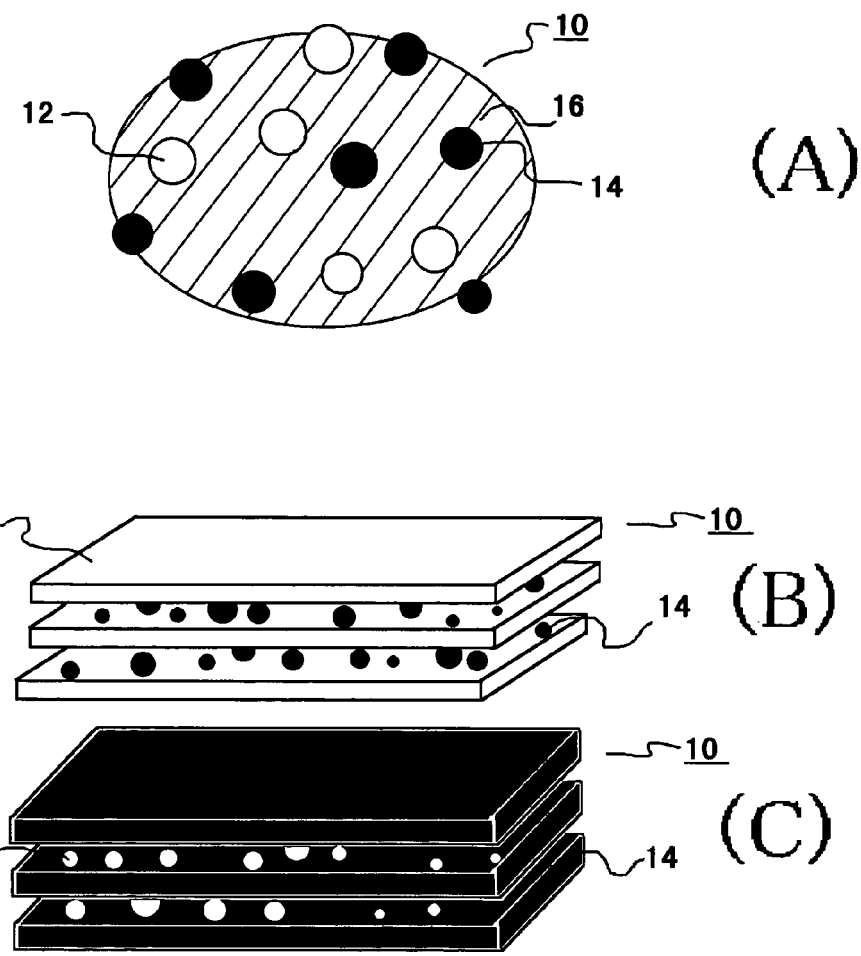
FIG. 2 is a view showing a different example of the structure of the composite powder according to this invention.
Figure 3:
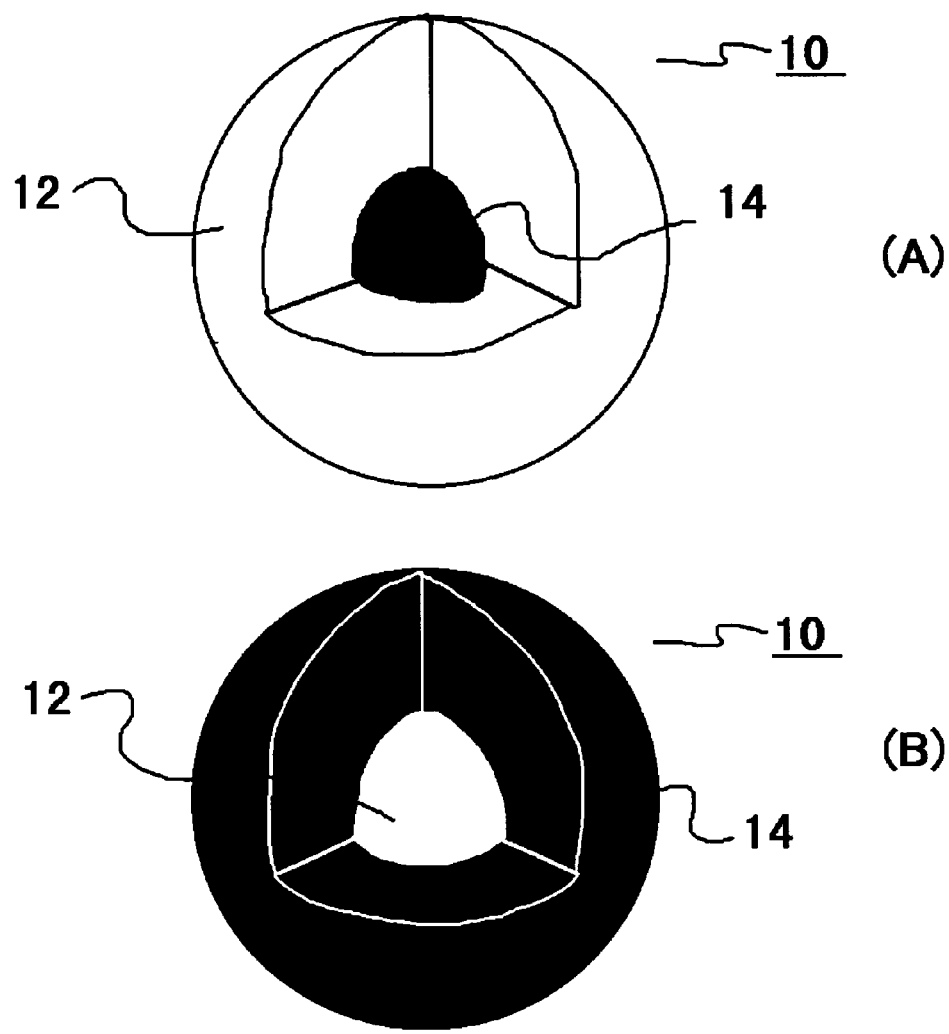
FIG. 3 is a view showing a different example of the structure of the composite powder according to this invention.

Further, examples of the composite powder 10 of the present invention include various types of composite powder which are: composite powder 10 in which an acting site 14 and an adsorbing site 12 are formed on a base powder 16 (FIG. 2A); the composite powder in which an acting site14 is carried between layers of adsorbing site 12 (FIG. 2B) (or composite powder in which adsorbing site 12 is carried between layers of acting site 14 (FIG. 2C)), and the composite powder 10 in which acting site 14 is encapsulated in an adsorbing site 12 (FIG. 3A) (or composite powder in which an adsorbing site 12 is encapsulated in acting site 14 (FIG. 3B). However, as far as the effect of the present invention is not deteriorated, the structure of composite powder10 is not particularly limited.

In the composite powder, it is preferable that the covering amount and the covering rate are adjusted, so that such structure is obtained that acting effect at the acting site can be sufficiently exerted, and adsorbing effect at the adsorbing site is not prevented.

Adsorbing Site

In the composite powder of the present invention, an adsorbing site is determined by a relationship with an enzyme to be adsorbed, and is preferably assessed by correlation with the zeta-potential of a subject enzyme.

When a powder has a charge in a liquid, an ion with the opposite charge is attracted to the powder by an electrostatic force in order to cancel this charge, and to form an electric double layer. A potential on an outermost side of a double layer is a zeta-potential. Therefore, the zeta-potential is suitably used for assessing surface charge state of a subject, and ability to electrically adsorb an enzyme can be assessed.

The zeta-potential is obtained by Smoluchowski's equation:

$$\text{Zeta-potential} = 4\pi\eta U/\epsilon$$

($\eta$:viscosity of solvent, U:electrophoresis mobility, $\epsilon$:inductivity of solvent).

In order to obtain the zeta-potential, a speed (V) and an electrophoresis mobility (U) of a colloid particle are obtained by an electrophoresis method. When electric field (E) is applied to a charged colloid particle, a particle is moved. V and U are obtained by V=L/t (L: moved distance, t: time) and U=V/E.

When a subject enzyme is plasminogen activator with a positive value of the zeta-potential, it is preferable that the zeta-potential of a substance constituting an adsorbing site exhibits a negative value at pH on a skin. In addition, the zeta-potential value of a substance constituting an absorbing site exhibits preferably −10 mV or lower, more preferably −15 mV or lower, most preferably −20 mV or lower at pH 7.5.

A method of measuring the zeta-potential is as follows:

A sample was dispersed in a Tris-HCl buffer of pH7.5, and subjected to ultrasonic treatment, which was used for measurement. The zeta-potential is measured using an electrophoresis light scattering photometer LEZA-600 manufactured by Otsuka Electronics Co., Ltd. Measurement is performed three times, and the result is expressed as an average value thereof.

A relationship between the zeta-potential of a main substance at pH 7.5, and UK (urokinase which is one of PA) adsorption rate at the concentration of 100 ppm is shown below.

| Sample | Zeta potential (mV) | UK adsorption rate (%) |
|---|---|---|
| Inorganic powder | | |
| Silica (SUNSPHERE L ™) | −20.0 | 82 |
| Mica (EIGHT PEARL 300S ™) | −18.9 | 79 |
| Talc (Talk JA-68R ™) | −19.3 | 78 |
| Zinc oxide (ZINC WHITE SEIDO) | +5.5 | 29 |
| Alumina (MAX LIGHT A100 ™) | +17.3 | 0 |
| Organic powder | | |
| Polyamide (NYLON SP500 ™) | −32.0 | 34 |
| Polymethyl methacrylate (GANZPEARL ™) | −18.0 | 42 |
| Silicone resin (TOSPEARL 145A ™) | −14.0 | 30 |
| Ethyl carbamate (PLASTIC POWDER ™) | −13.0 | 27 |
| Organo polysiloxane extremer spherical powder (TREFIL E506S ™) | −12.0 | 18 |
| Cellulose (CELLUFLOW C-25 ™) | −2.0 | 21 |
| Polyethylene (FLO-THENE UF ™) | +1.0 | 10 |

A method of measuring UK adsorption rate is as follows:

A Tris-HCl buffer (pH7.5) was added to 20 μL of a suspension of a sample in water to a total amount of 180 μL, and 20 μL of 10 μg/mL precursor-type UK was added thereto, and allowed to stand at room temperature for 5 minutes. Thereafter, the sample powder was filtered, and the filtrate was recovered. Further, the powder was sufficiently washed with a constant amount of Tris-HCl buffer, and the filtrate and the washing solution were combined, which was used as an unadsorbed UK solution. The UK concentration in the unadsorbed UK solution is obtained by ELISA method using TintEliza uPA (biopool), an amount of UK adsorbed onto a sample powder was calculated and a UK adsorption rate is obtained.

There is a tendency that as the zeta-potential is lower, a UK adsorption rate is higher, and it was shown that there is a relationship between the zeta-potential and a UK adsorption rate although among each organic powder or each inorganic powder there is not necessarily proportional relationship.

Therefore, as preferable substances for an adsorbing site, inorganic powders such as silica, mica, talc and so on; organic powders such as polyamide, polymethyl methacrylate, silicone resin and so on are specifically listed.

An adsorbing site may be composed of 1 or more than 2 substances.

Acting Site

In the composite powder of the present invention, an acting site is also determined by a relationship with an enzyme of an action subject.

In the case where the subject enzyme is plasminogen activator, it is preferable that, as a main component of an acting site, a metal or a metal compound from which a zinc ion is dissolved out is used.

Examples of a metal compound from which zinc ion is dissolved out include inorganic compounds in a form (complex) including oxide, hydroxide, nitrate, chloride, hydrate, carbonate, bicarbonate, sulfate, borate, persulfate and an inorganic compound (complex) containing them in the molecule; organic acid salts such as glycerophosphate, acetate, hydroxide and α-hydroxy acid (citrate, tartrate, lactate, malate) or fruit acid salt, amino acid salt (asparate, alginate, glycolate, fumarate) or fatty acid salt (palmitate, oleate, caseinate, behenate). When the composite powder of the present invention is used in a skin external preparation, examples of a particularly preferable metal compound include zinc oxide and/or zinc basic carbonate.

Then, UK inhibiting rates of ions at the ion concentration of 100 ppm are shown.

| Sample | UK active inhibition rate (%) |
|---|---|
| $Zn^{2+}$ | 52 |
| $Zr^{4+}$ | 45 |
| $Cu^{2+}$ | 36 |
| $Ni^{2+}$ | 30 |
| $Co^{2+}$ | 27 |
| $Al^{3+}$ | 16 |
| $Ce^{3+}$ | 5 |
| $Na^+, Li^+, K^+, Mn^{2+}, Ba^{2+},$ $Mg^{2+}, Ba^{2+}, Ca^{2+}$ | 0 |

A method of measuring a UK activity inhibiting rate is as follows:

A Tris-HCl buffer (pH7.5) was added to 20 μL of a suspension of a sample in water to a total about of 180 μL, 20 μL of 300 U/mL active type UK is added thereto, and is allowed to stand at room temperature. After 30 minutes, 20 μL of S2444 (CHROMOGENIX) which is a specific synthetic substrate for UK is added, and is further allowed to stand in a 37° C. thermostat for 30 minutes. Thereafter, 20 μL of a 12% aqueous trichloroacetic acid solution is added to stop the reaction, a sample powder is filtered, absorbance of the filtrate at 405 nm is measured to obtain UK activity in an assessment system, and a UK activity inhibiting rate of the sample is calculated.

Action of each ion on an enzyme has high specificity, and most excellent UK inhibiting activity is confirmed in zinc ion.

Further, when antibacterial and antifungal effect is considered, it is preferable that the aforementioned zinc oxide and/or zinc basic carbonate is a main component, and this contains 1 or more than 2 alkali metal salts selected from hydroxide, hydrogencarbonate and, as carbonate of lithium, sodium and potassium as a mixture. In addition, it is preferable that an alkali metal salt is particularly sodium carbonate or potassium carbonate.

Inert Powder

As described above, the composite powder of the present invention may have a structure in which an adsorbing site and an acting site are formed on an inert powder (FIG. 2A). An inert powder is not particularly limited as far as the effect of the present invention is not deteriorated, and an inorganic base powder, an organic base powder, an inorganic pigment base powder, and a organic pigment base powder can be used.

Complex Effect

In a normal skin, PA is localized in the corneal layer and dermis. However, it is known that, by skin roughening and various skin diseases accompanied with keratinization abnormality, PA is activated, suitable localization of PA in the skin is disordered, and diffusion of PA is occurred.

The reason why activation and diffusion of PA are inhibited by the composite powder of the present invention can be supposed as follows:

A substance with a negative zeta-potential value is excellent in ability to electrically adsorb PA. When the composite powder having an adsorbing site with a negative zeta-potential value is coated on skin, a large amount of PA produced in the skin cell is attracted to the adsorbing site, and is localized in an upper layer part of an epidermis. That is, PA is adsorbed on an adsorption site of the composite powder, and diffusion is inhibited.

And, activation of PA adsorbed onto the adsorbing site of the composite powder is inhibited by PA inhibiting effect of the acting site.

When trypsin that is classified into the same category of serine protease as PA was studied as a reference, activity of trypsin was hardly lost. That is, an acting site of the present invention does not inhibit enzyme activity non-specifically.

In PA, there are two kinds of urokinase (UK) and tissue type (PA). The former is a healthy epidermis, and the latter is recognized of its existence in a morbid epidermis mainly.

A representative of the composite powder of the present invention has inhibitory activity on both of these PAs. It is preferable that PA inhibiting rate is 40% or more particularly 50% or more.

Even when powders constituting each site of the composite powder are mixed in the powder state, higher effect than that of each powder alone is exerted depending on the condition in some cases. However, in a composite powder in which a site having inhibitory activity on these specified enzymes, and an adsorbing site are exposed on a surface, since movement of a particle does not occur, an adsorbing site can continue to have stably a negative zeta-potential, and extremely high enzyme activity, for example, PA inhibiting effect is confirmed.

In addition, since the composite powder of the present invention uses zinc oxide and/or zinc basic carbonate obtained by combing alkali metal salts as an acting site, excellent antibacterial and antifungal effect is obtained as compared with zinc oxide which is a currently generally used inorganic antibacterial agent. In addition, since zinc oxide and/or zinc basic carbonate and alkali metal salt are sufficiently mixed, and an alkali metal salt is encapsulated in a fine aggregate of zinc oxide and/or zinc basic carbonate, antibacterial and antifungal activity can be continued for a long period, which is different from the case of mixture of two agents in the powdery state.

The Process of Making the Composite Powder

Figure 4:
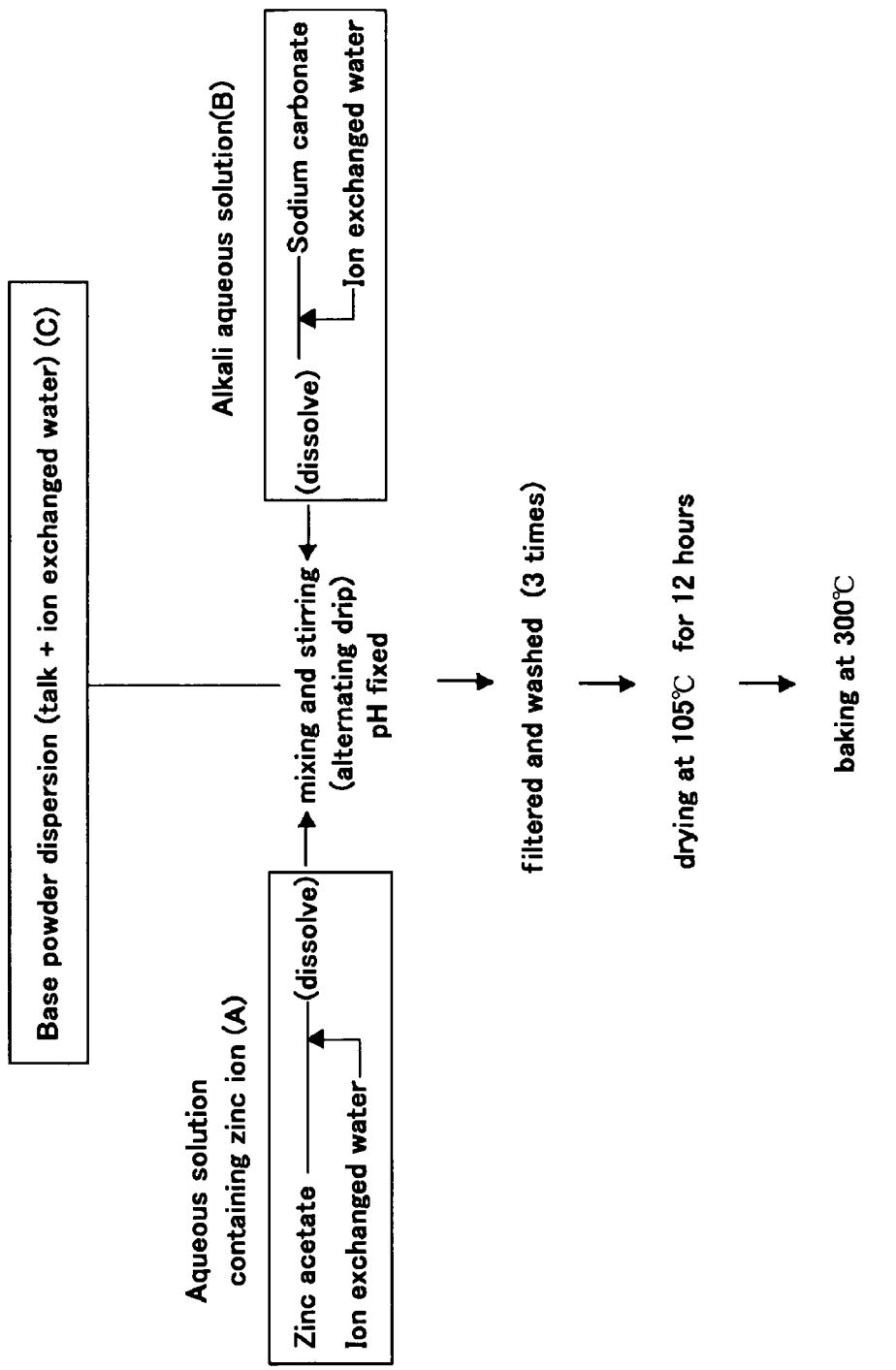
FIG. 4 is a view showing an example of the process of making the composite powder according to this invention.

An example of the process of making is shown in FIG. 4.

In this method, a composite powder can be effectively obtained by using a base powder dispersion in addition to an aqueous solution containing a zinc ion and an alkali aqueous solution, and reducing a time of water washing at a water washing step, in the aforementioned method of synthesizing zinc oxide and/or zinc basic carbonate, whereby, an alkali metal salt adsorbed onto a fine particle of zinc oxide or zinc basic carbonate dispersed in the reaction solution is intentionally made to remain.

First, an aqueous solution containing zinc ion, an alkali aqueous solution, and a base powder dispersion are prepared. In FIG. 4, as a base powder dispersion (C), talc is used by dispersing in ion-exchanged water. Further, as an aqueous solution containing a zinc ion (A), an aqueous zinc acetate solution is used and, as an alkali aqueous solution (B), an aqueous sodium carbonate solution is used.

An aqueous solution (A) containing zinc ion and an alkali aqueous solution (B) are supplied to a reactor containing a base powder dispersion (C) under room temperature and atmospheric pressure while amounts are adjusted so that pH of a reaction solution is retained constant 7 to 10, and the materials are mixed and stirred. Thus obtained product can be centrifuged to filter it, washed with water, dried, and baked. In an example of the process shown in FIG. 4, drying was performed at 105° C. for 12 hours in a drying step, and baking was performed at 300° C. in the baking step. In addition, in order to adjust a particle diameter of the powder, grinding treatment may be performed after baking.

In synthesis of a composite powder, pH is preferably 7 to 10. When pH in the synthesis is lower than 7 or exceeds 10, there is a possibility that antibacterial and antifungal activity is not exerted.

As a raw material for an aqueous solution containing a zinc ion, inorganic acid salts such as zinc sulfate, zinc nitrate, zinc phosphate, zinc halide; organic acid salts such as zinc formate, zinc acetate, zinc propionate, zinc lactate, zinc oxalate, zinc citrate can be used.

In the present invention, it is particularly preferable to use zinc acetate, zinc sulfate or zinc chloride. Further, when zinc sulfate or zinc chloride is used, it is preferable to add acetic acid whose mol number is 2-fold of mol number of zinc contained in the material. When these synthetic raw materials are used, antibacterial and antifungal effect becomes particularly excellent.

As a raw material for an alkali aqueous solution, hydroxide, hydrogencarbonate, and carbonate of lithium, sodium, and potassium can be used. In the present invention, it is particularly preferable to use sodium carbonate or potassium carbonate.

The process for preparing the composite powder of the present invention is not limited to the aforementioned process, but any process can be applied as far as the effect of the present invention is not deteriorated.

For example, zinc oxide is directly synthesized without via zinc basic carbonate using an aqueous solution of a strong alkali such as sodium hydroxide and potassium hydroxide in place of an alkali aqueous solution containing a carbonate ion, and this can be washed with water, filtered and dried to obtain a composite powder.

Alternatively, water washing is sufficiently performed in a water washing step of the aforementioned step, to synthesize a preliminary powder (complex aggregate of zinc oxide and base powder) not substantially containing impurities other than a base powder and zinc oxide, and the powder is immersed in an aqueous solution containing an alkali metal salt, and dried, whereby, an alkali metal salt can be uniformly mixed in an alkali metal salt in a preliminary powder.

In the composite powder of the present invention, it is preferable that a content of zinc oxide and/or zinc basic carbonate is 5 to 75% by weight relative to a composite powder. When the content is less than 5% by weight, desired effect cannot be obtained in some cases and, when the content exceeds 75% by weight, spreading becomes difficult, and there is a possibility to deteriorate the usability when it is blended in cosmetic compositions.

In addition, in the composite powder of the present invention, it is preferable that a content of an alkali metal salt is 0.5 to 50% by weight of whole composite powder. When the content is less than 0.5% by weight, desired antibacterial and antifungal effect is not obtained in some cases, being not preferable. On the other hand, when the content exceeds 50% by weight, although initial antibacterial activity is shown well, the activity of a composition is deteriorated due to high hygroscopicity and dissolution out property of an alkali metal salt for elution out, or an antibacterial agent itself becomes strongly alkaline, being not preferable.

In addition, in the composite powder of the present invention, since an alkali metal salt is present, excellent antibacterial and antifungal effect is obtained as compared with zinc oxide, which is a currently generally used inorganic antibacterial agent. In addition, since zinc oxide and/or zinc basic carbonate and alkali metal salt are sufficiently mixed and an alkali metal salt is embedded in a fine aggregate of zinc oxide and/or basic zinc oxide, antibacterial and antifungal activity can be continued for long period unlike a mixture of the two powders in the simple powdery state.

Further, by combining a base powder having better usability, spreading becomes easy when blended in cosmetic compositions.

In addition, it is preferable that pH of 10% by weight aqueous dispersion of the synthesized composite powder is 9 to 14, particularly 9.5 to 12. When pH of an aqueous dispersion is less than 9, there is a possibility that antibacterial and antifungal activity in not exerted.

By inclusion of the aforementioned composite powder, the cosmetic composition of the present invention exhibits comprehensively excellent property over versatile elements such as antibacterial and antifungal property, safety and usability. And, since a preferable composite powder in the present invention does not use expensive raw material such as silver and zinc-substituted zeolite, the complex power is relatively inexpensive as compared with the former inorganic antibacterial agent. In addition, unlike an agent utilizing photocatalystic function, antibacterial and antifungal effect can be also expected in dark place, and the composite powder has an advantage that an antibacterial agent alone or a composition containing an antibacterial agent has little change with time, which was frequently problematic in the former antibacterial agent. Further, to mention specially, the composite powder exhibits high effect also on fungus such as mold and yeast against which the former inorganic antibacterial and antifungal agent has low effect. Thereby, the amount of an antiseptic such as paraben and sodium dehydroacetate, which are generally used in cosmetic compositions to be blended, can be reduced, and cosmetic compositions without paraben, sodium dehydroacetate and so on have become possible. Although cosmetic compositions such as mascara that are generally used around eyes require strong antiseptic effect, the amount of paraben is reduced, and the amount of an alcohol to be blended is suppressed by blending the aforementioned composite powder, whereby stimulation to the mucosa can be reduced.

A content of the composite powder of the present invention contained in the cosmetic of the invention is not particularly limited as far as the effect of the invention can be obtained in the amount range, which can be used by appropriately adjusting the amount. But the range is generally 0.5 to 60% by weight. When the content is less than 0.5% by weight, there is a possibility that the effect of the invention is not exerted. In some cases when the content exceeds 60% by weight, it is not preferable from a viewpoint of preparation formulation.

Ingredients mentioned below which are used in normal cosmetic compositions, for examples moisturizing agents, antioxidants, oil components, ultraviolet absorbers, emulsifiers, surfactants, thickeners, alcohols, powder components, color materials, aqueous components, water, various kinds of skin nutrition agents and so on can be appropriately blended in the cosmetic of the present invention in such a range that the effect of the present invention is not deteriorated Further, sequestering agents such as disodium edentate, trisodium edentate, sodium citrate, poly sodium phosphate, metasodium phosphate, gluconic acid, malic acid and so on; various crude drug extracts such as caffeine, tannin, verapamil, tranexamic acid and also the derivatives, licorice, Chinese quince, shinleaf and so on; agents such as tocopherol acetate, glycyrrhetinic acid, glycyrrhizinic acid and also the derivatives or the salts and so on; whitening agents such as vitamin C, magnesium ascorbate phosphate, ascorbic acid glucoside, arbutin, kojic acid and so on; amino acids such as arginine, lysine and also the derivatives; saccharides such as fructose, mannose, erythritol, trehalose, xylitol and so on can be also appropriately blended therein.

The cosmetic of the present invention can be applied in any form which is used in the conventional cosmetic compositions, such as ointment, cream, milky lotion, lotion, pack, foundation, cheek rouge, eye shadow, face powder, lipstick, bath medicine, oil removing paper, paper face powder, body powder, baby powder, powder spray and so on, a dosage form being not limited.

Application of the composite powder of this invention to sensitive skin, for which use of the former cosmetic compositions are difficult, show excellent effect mentioned in the present invention.

A sensitive skin is defined in publications as follows:

"A skin usually susceptible to a damage due to a specific response to quasi-drugs, cosmetics, plants, ultraviolet ray, metals to which most of human beings do not respond particularly."

"A skin which is sensitive constitutionally to an allergenic substances (pollen, fragrance) or irritative substances (alcohols) due to a reduced barrier function of skin."

"A skin susceptible to a damage by an irritating substance only temporarily when the resistance of skin or the physiological functions of skin are deteriorated due to an insufficient sleep, overwork, menstruation, seasons change, mental stress and the like."

"A skin posing an anxiety about the use of cosmetics used routinely."

Thus, factors for sensitive skin condition are reduced skin barrier function, reduced skin irritation threshold, skin dryness, substance causing contact dermatitis, physicochemical irritation, stress, physical condition, seasons change, ultraviolet ray, menstruation and the like. It is also possible that one's mistaken skin care itself causes a sensitive skin and that one's obsession just causes sensitive skin.

In the present invention, subject person having a sensitive skin is defined as the person recognized abnormal felling in any of the procedures (1) to (5) shown below.

(1) 100 µl of 5% aqueous solution of citric acid is applied over the cheek and allowed to stand for 10 minutes.

(2) 100 µl of 5% aqueous solution of lactic acid is applied over the cheek and allowed to stand for 10 minutes.

(3) 100 µl of 50% ethanol solution is applied over the cheek and allowed to stand for 10 minutes.

(4) An unwoven fabric (2×2 cm) is impregnated with 100 µl of 0.2% aqueous solution of methylparaben, and allowed to stand on the cheek for 10 minutes.

(5) An unwoven fabric (2×2 cm) is impregnated with 100 µl of 5% aqueous solution of SDS, and allowed to stand on the cheek for 10 minutes.

The abnormal felling means relatively painful feeling on skin, such as tingling pain, creepy feeling, itching sensation, feverish feeling, discomfort, sting pain and the like.

Further, the composite powder of the present invention can be blended into all articles and member subjects which are directly contacted with a human skin, or may generate friction, such as paper articles and office supplies such as tissue paper, paper towel, napkin, bill, coupon, ticket, book, poster, newspaper, magazine, notebook, memo pad and so on; clothes such as lingerie, underwear, shirts, lining cloth of hats or shoes, socks, sandals and so on; childcare and nursing supplies such as paper diaper for babies and infants and aged and so on; daily necessaries such as sanitary products, contraceptive devices, kitchen sponges, scrubbing brushes, toilet seat, toilet seat covers, dustcloths, toothbrushes, masks, medical use gauzes, band aids, medical use supporter, softening agent, clothing use detergent and so on; furniture and bedclothes such as chair, bed, bedding, blanket, Japanese cushion, pillow and their coverings, cabinet, curtain, carpet and so on; construction members such as wallpaper, wall material, floor material, pillar, handrail and so on; sport supplies such as handle and knob of baby car, cart, electric appliance, tableware, and shelf and so on; tape for sports, supporter for sports and so on; grips and groves of various sport supplies such as golf, tennis, table tennis and skiing, bats and gloves of baseball, and various protectors of rugby and football and so on; members such as vehicle sheets, strap, handle, interior articles of automobile, bicycle, bus, electric car and airplane and so on.

By blending the composite powder of the present invention, utilities as a functional raw materials which are very safe, highly reliable, effective on antibacterial and antifungal action, and effective on skin roughening suppressing or improving action are expected in daily lives, sport scenes or medical conducts.

EXAMPLE 1

Ion-exchanged water is placed into a reaction vessel, and 100 g of talc (JA-68R™: manufactured by ASADA SEIFUN CO., LTD., zeta-potential:–19.3 mV) is dispersed therein. To this were connected two microtube pumps, and pH controller and a stirring apparatus were set. Two microtube pumps were connected to each of a solution in which 33.4 g of zinc chloride and 29.6 g of acetic acid were dissolved in 160 mL of ion-exchanged water, and a solution in which 88.4 g of anhydrous sodium carbonate was dissolved in 270 mL of ion-exchanged water, and fixed, so that each solution can be added dropwise to the reaction vessel. A reaction was performed by adjusting adding amounts of the two aqueous solutions, while stirring under atmospheric pressure and room temperature, and kept constantly pH8 during the reaction. An addition dropwise time was about 30 minutes. The resulting precipitates were washed with water, and filtered three times repeatedly, dried in an oven at 105° C. for 12 hours, ground with a personal mill, and baked at 300° C. for 1 hour. This powder was passed through a 60 mesh sieve after grinding, to obtain an objective material.

EXAMPLE 2

According to the same procedure as that of Example 1 except that mica (Eight pearl 300S™: manufactured by KAKUHACHI CO., LTD., zeta-potential: –18.9 mV) was used in place of talc in Example 1, an objective material was obtained.

EXAMPLE 3

According to the same procedure as that of Example 1 except that silica (CHEMISELEN™: manufactured by SUMITOMO CHEMICAL CO., LTD., zeta-potential: –39.4 mV) was used in place of talc in Example 1, an objective material was obtained.

EXAMPLE 4

Omitting the baking step in Example 1, a composite powder of zinc basic carbonate was obtained.

EXAMPLE 5

According to the same procedure as that of Example 1 except that Alumina (MAX LIGHT A100™: manufactured by SHOWA DENKO K. K., zeta-potential: +17.3 mV) was used in place of talc in Example 1, an objective material was obtained.

EXAMPLE 6

According to the same procedure as that of Example 1 without blending talc, a composite of zinc oxide and sodium carbonate is obtained. 10 g of this composite and 50 g of talc were uniformly stirring to mix with a small size mixer to obtain an objective mixture.

EXAMPLE 7

Zinc oxide on the market (manufactured by SEIDO CHEMICAL CO.,LTD)

EXAMPLE 8

Inorganic type antibacterial agent on the market (ZEOMIC™: manufactured by SINANEN ZEOMIC CO., LTD)

EXAMPLE 9

Talc (JA-68R™: manufactured by ASADA SEIFUN CO., LTD)

EXAMPLE 10

Mica (EIGHT PEARL 300S™: manufactured by KADOHACHIGYORINHAKU CO., LTD)

EXAMPLE 11

Silica(CHEMISELEN™: SUMITOMO CHEMICAL K.K.)

1. Antibacterial and Antifungal Activity Test

Figure 5:
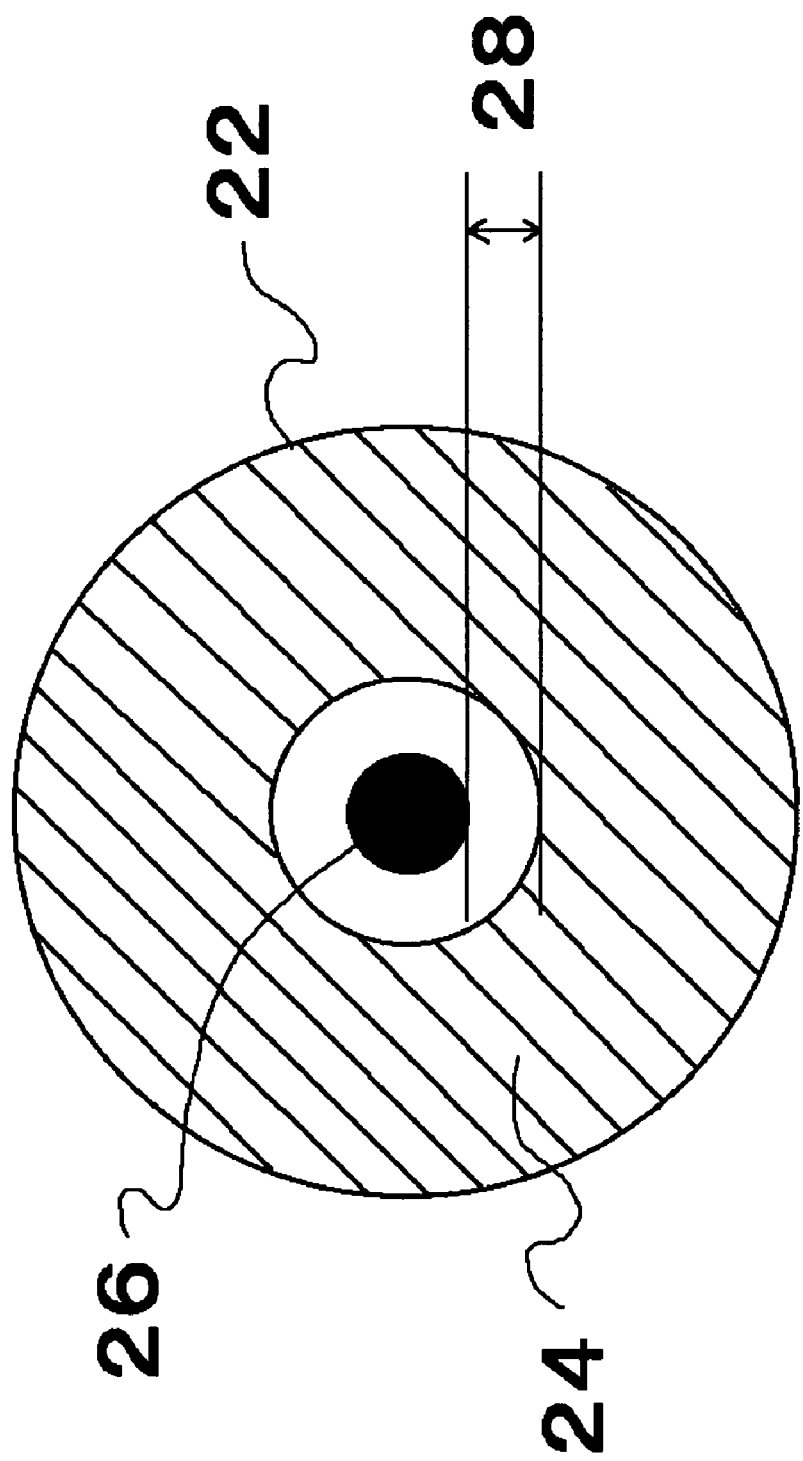
FIG. 5 is a view showing the evaluation method of the antibacterial activity of the composite powder according to this invention.

FIG. 5 is a view for explaining a method of assessing antibacterial and antifungal activity. For the test of fungi, a potato dextrose agar medium was used, and for the test of bacteria, room bouillon agar medium was used. As shown in FIG. 5, a medium 24 is made in a laboratory dish 22, and each test bacterial strain of fungi[Blue mold (*Penicillium* sp.), Black mold (*Aspergillus niger*), *Candida albicans* (*Candida albicans* ATCC10231)]; and bacteria [*Pseudomonas aeruginosa* (*Pseudomonas aeruginosa* ATCC15442), *Escherichia coli* (*Escherichia coli* ATCC8739), *Staphylococcus aureus* (*Staphylococcus aureus* FDA209P), Acne germ (*P.acnes* JCM6473)] is coated on the medium 24. A sample 26 obtained by compressing and molding each powder of Example 1 to 11 into a disc of 8 mm diameter with a pharmacy compressing machine is disposed on a center of the medium 24, a fungus is cultured at 25° C. for 72 hours, a bacterium is cultured at 30° C. for 48 hours, and activity thereof was assessed by a width 28 of a growth inhibiting band, in which growth of each fungus or bacterium was inhibited, formed around a sample 26 on the medium 24 after a predetermined time. It can be estimated that as a width 28 of a growth inhibiting band is wider, antibacterial and antifungal activity is excellent. And, activity was assessed by evaluation criteria as shown in Table 1.

2. Measurement of PA Inhibitory Activity

A Tris-HCl buffer (pH 7.5) was added to each 20 μL of a suspension of a powder of Example 1 to 11 to a total amount of 180 μL, and 20 μL of 300 U/mL active-type urokinase (UK) was added thereto, and allowed to stand at room temperature. After 30 minutes, 20 μL of S2444 (CHROMOGENIX) which is a synthetic substrate specific for UK was added, and this was further allowed to stand in a thermostat at 37° C. for 30 minutes. Thereafter, 20 μL of a 12% aqueous trichloroacetic acid solution was added to stop the reaction, a sample powder was filtered, absorbance of the filtrate at 405 nm was measured to obtain PA activity in the estimating system, and the PA inhibiting rate of a sample was calculated. When the PA inhibiting rate is 40% or higher, it is estimated that there is PA inhibiting activity. UK is one kind of PA as described above.

The result is shown in Table 2.

TABLE 1

Evaluation criteria

| Evaluation | Width of the growth prevention band of fungi | Width of the growth prevention band of bacteria |
|---|---|---|
| A | 15.0 mm or more | 7.5 mm or more |
| B | 10.0 mm or more less than 15.0 mm | 5.0 mm or more less than 7.5 mm |
| C | 5.0 mm or more less than 10.0 mm | 2.5 mm or more less than 5.0 mm |
| D | Less than 5.0 mm | Less than 2.5 mm |
| E | 0 mm (without inhibiting band) | 0 mm (without inhibiting band) |

TABLE 2

| Example | PA inhibiting rate (%) | Antibacterial and antifungal activity | | | | | | |
|---|---|---|---|---|---|---|---|---|
| | | (1) | (2) | (3) | (4) | (5) | (6) | (7) |
| 1 | 51 | A | A | A | B | B | A | A |
| 2 | 55 | A | A | A | C | B | A | A |
| 3 | 53 | A | A | A | C | B | A | A |
| 4 | 47 | A | A | B | C | B | A | A |
| 5 | 28 | A | A | A | C | C | A | A |
| 6 | 26 | A | A | A | C | C | A | A |
| 7 | 34 | E | D | D | E | D | D | C |
| 8 | 18 | D | D | D | B | B | B | B |
| 9 | 15 | E | E | E | E | E | E | E |
| 10 | 16 | E | E | E | E | E | E | E |
| 11 | 20 | E | E | E | E | E | E | E |

(1) Blue mold
(2) Black mold
(3) *Candida albicans*
(4) *Pseudomonas aeruginosa*
(5) *Escherichia coli*
(6) *Staphylococcus aureus*
(7) Acne germ Regarding Antibacterial and Antifungal Activity Example 7 with only zinc oxide was inferior in both of antibacterial and antifungal activity as compared with Examples 1 to 4, which are using the composite powder of the present invention. From this, it was seen that although zinc oxide was originally known as an inorganic antibacterial substance, sufficient antibacterial and antifungal activity cannot be obtained only with itself and, by combining an alkali metal salt with zinc oxide, antibacterial and antifungal activity is improved. In addition, also in Example 8, which is a commercially available inorganic antibacterial agent, antibacterial and antifungal activity was inferior as compared with Examples 1 to 4 which are using the composite powder of the present invention.

In addition, also in the composite of zinc basic carbonate without a firing step (Example 4), the same effect as that of the composite of zinc oxide (Examples 1 to 3) was recognized.

Further, in Example 5 using alumina having a positive zeta-potential, antibacterial and antifungal activity against *Escherichia coli* was lower as compared with Examples 1 to 4 using talc, mica or silica having a negative zeta-potential. In addition, also in Example 6 in which a composite of zinc oxide and alkali metal salt, and talc were merely mixed, antibacterial and antifungal activity against *Escherichia coli* was low.

Regarding PA Inhibitory Activity

In Example 5 using alumina having a positive zeta-potential as an adsorbing site, a PA inhibiting rate was lower as compared with Examples 1 to 4 using talc, mica or silica having a negative zeta-potential as an adsorbing site. This can be thought that because of positive zeta-potential, PA cannot be adsorbed.

In addition, also in Example 7 with only zinc oxide, a PA inhibiting rate was inferior. From this, it was seen that although zinc oxide was originally known to have skin roughening improving effect, sufficient PA inhibiting activity cannot be obtained only with itself and, by combining with an adsorbing site having PA adsorbing activity, PA inhibiting effect is improved.

In addition, in Examples 9 to 11 using talc, mica, or silica alone, a PA inhibiting rate was inferior. Therefore, it was confirmed that PA inhibitory activity can not be obtained by adsorbing site only.

In addition, in Example 6 in which merely mixing an acting with talc acted as an adsorbing site causes a low PA inhibiting rate, and it was confirmed that, by combining an adsorbing site with an acting site as shown in Examples 1 to 4, remarkable improvement of the inhibiting rate was seen. This is thought that merely mixing an adsorbing site with an acting site causes movement of a particle, so that an adsorbing site can not have a negative potential stably.

Therefore, it was confirmed that antibacterial and antifungal effect of the composite powder of the present invention is improved by combining zinc oxide with a salt of an alkali metal. In addition, the composite powder has effect also on acne bacterium, and has effect of inhibiting pimple. Further, it was confirmed that, by combining an adsorbing site having a negative zeta-potential with an acting site, excellent PA inhibitory activity is exerted.

Then, a specific method of testing antibacterial and antifungal activity, stimulating property, and easy spreading of a cosmetic composition containing the composite powder of the present invention, as well as Evaluation criteria will be explained below.

Antibacterial and Antifungal Activity

Test method: Each sample is molded in an inner dish based on JIS Z2911 mold resistance test, a mold is sprayed, the dish is covered with a lid, and allowed to stand in a constant temperature incubator at 25° C. under moisturing condition, and the presence or the absence of growth of a mold is observed with naked eyes.

Evaluation Criteria

○: After 4 weeks, a hypha is not seen with naked eyes.
Δ: After 4 weeks, a hypha is slightly observed with naked eyes
×: After 4 weeks, a hypha is widely observed with naked eyes Stimulating Property Test method: A sample was coated on 20 panelists, and they were questioned whether they feel stimulation after 10 minutes.

Evaluation Criteria

○: No panelists felt stimulation.
Δ: 1 panelist felt stimulation.
×: 2 or more panelists felt stimulation.

Easiness of Spreading

Test method: function evaluation was performed by 20 specialist as panelists.

Evaluation Criteria

⊚(easy): 8 or more panelists felt easy.
○(slightly easy): 5 to 7 panelists felt easy.
Δ(slightly difficult): 2 to 4 panelists felt easy.
×(difficult): 1 or less panelist felt easy.

A process for preparing a cosmetic composition is as follows:

An oily phase part is mixed at 85° C., sprayed to an uniformly mixed powder part, and the materials are mixed with a blender.

Results are shown in Table 3.

TABLE 3

| Sample(wt %) | Blending example | | | | | | | | | |
|---|---|---|---|---|---|---|---|---|---|---|
| | 1 | 2 | 3 | 4 | 5 | 6 | 7 | 8 | 9 | 10 |
| Example 1 | 5 | — | — | — | — | — | — | — | — | — |
| Example 2 | — | 5 | — | — | — | — | — | — | — | — |
| Example 3 | — | — | 5 | — | — | — | — | — | — | — |
| Example 6 | — | — | — | — | — | — | — | — | — | 5 |
| Example 7 | — | — | — | 5 | — | — | — | — | — | — |
| Example 8 | — | — | — | — | 5 | — | — | — | — | — |
| Ethyl paraben | — | — | — | — | — | 0.5 | — | — | — | — |
| Talc | 20 | 20 | 20 | 20 | 20 | 20 | 25 | — | 20 | 20 |
| Mica | 63 | 63 | 63 | 63 | 63 | 67.5 | 63 | 5 | 63 | 63 |
| Silica | — | — | — | — | — | — | — | 5 | — | — |
| Dimethylpoly-siloxane | 1 | 1 | 1 | 1 | 1 | 1 | 1 | 1 | 1 | 1 |
| Diisostearyl malate | 5 | 5 | 5 | 5 | 5 | 5 | 5 | 5 | 5 | 5 |
| Glyceryl trioctanoate | 5 | 5 | 5 | 5 | 5 | 5 | 5 | 5 | 5 | 5 |
| Sorbitan sesquioleate | 1 | 1 | 1 | 1 | 1 | 1 | 1 | 1 | 1 | 1 |
| Antibacterial and anitfungal activity | ○ | ○ | ○ | × | × | ○ | × | × | × | ○ |
| Stimulating property | ○ | ○ | ○ | ○ | ○ | × | ○ | ○ | ○ | ○ |
| Easiness of spreading | ○ | ○ | ○ | × | × | ○ | ○ | ○ | ○ | × |

As apparent from Table 3, Blending Example 4 using commercially available zinc oxide, and Blending Example 5 using a commercially available antibacterial and antifungal agent had no stimulation, but were inferior in antibacterial and antifungal activity, and easy spreading property. Blending Example 6 using ethylparaben had antibacterial and antifungal activity and easy spreading, but was inferior in stimulation. Blending Examples 1 to 3 using the composite powder of the present invention exhibited sufficient antibacterial and antifungal activity without blending ethylparaben, and had easy spreading property, and no stimulation.

In addition, it was seen that cosmetic composition in Blending Examples 1 to 3 using the composite powder of the present invention also exhibit antibacterial and antifungal activity to acne bacterium, and are also effective on a pimpled skin.

In addition, powders obtained in Examples 1 to 4 were analyzed by fluorescent X-ray, X-ray diffraction and infrared absorption spectroscopy indicated that the acting site is composed of zinc oxide as a main ingredient, together with 2 to 15% by weight of sodium carbonate.

Study of Synthetic Raw Material for Zinc Oxide and/or Zinc Basic Carbonate

Subsequently, the influence of difference in raw zinc compound for zinc oxide and/or zinc basic carbonate which is contained in the acting site studied on PA inhibitory activity and antibacterial and antifungal activity.

EXAMPLE 12

Ion-exchanged water is placed into a reaction vessel, and 100 g of talc (JA-68R™: manufactured by ASADA SEIFUN CO., LTD., zeta-potential:−19.3 mV) is dispersed thererin. To this were connected two microtube pumps, and pH controller and a stirring apparatus were set. Two microtube pumps were connected to each of a solution in which 50.1 g of zinc chloride and 44.4 g of acetic acid were dissolved in 240 mL of ion-exchanged water, and a solution in which 130 g of anhydrous sodium carbonate was dissolved in 400 mL of ion-exchanged water, and fixed, so that each solution can be added dropwise to the reaction vessel. A reaction was performed by adjusting amounts of two aqueous solutions to be added dropwise, while stirring under atmospheric pressure and room temperature, and kept constantly pH10 during the reaction. An addition dropwise time was about 30 minutes. The resulting precipitates were washed with water, and filtered three times repeatedly, dried in an oven at 120° C. for 12 hours, ground with a personal mill, and fired at 450° C. for 1 hour. This powder was passed through a 60 mesh sieve after grinding, to obtain an objective material.

EXAMPLE 13

According to the same procedure as that of Example 12 except that "59.3 g of zinc sulfate" was used in place of "50.1 g of zinc chloride" in Example 12, an objective material was obtained.

EXAMPLE 14

According to the same procedure as that of Example 12 except that "81.0 g of zinc acetate" was used in place of "50.1 g of zinc chloride and 44.4 g of acetic acid" in Example 12, an objective material was obtained.

EXAMPLE 15

According to the same procedure as that of Example 12 except that acetic acid was removed.

EXAMPLE 16

According to the same procedure as that of Example 12 except that "24.5 g of sodium hydroxide" was used in place of "130 g of anhydrous sodium carbonate" in Example 12, and that acetic acid was removed, an objective material was obtained.

EXAMPLE 17

According to the same procedure as that of Example 12 except that "90 g of anhydrous sodium carbonate" was used in place of "130 g of anhydrous sodium carbonate" in Example 12, and that acetic acid was removed, an objective material was obtained.

PA inhibitory activity and antibacterial and antifungal activity of powders obtained in Examples 12 to 16 were tested by the above method and criteria.

The result is shown in Table 4.

TABLE 4

| Example | PA inhibiting rate (%) | Antibacterial and antifungal activity | | | | | |
|---|---|---|---|---|---|---|---|
| | | (1) | (2) | (3) | (4) | (5) | (6) |
| 12 | 52 | A | A | A | A | A | A |
| 13 | 51 | A | A | A | B | A | A |
| 14 | 53 | C | B | A | D | D | D |
| 15 | 52 | E | D | D | E | D | D |
| 16 | 51 | E | D | D | E | D | D |

(1) Blue mold
(2) Black mold
(3) *Candida albicans*
(4) *Pseudomonas aeruginosa*
(5) *Escherichia coli*
(6) *Staphylococcus aureus*

It was apparently seen from Table 4 that in each example, PA inhibiting rate was excellent. In addition the powders of Examples 12 to 14 have excellent antibacterial and antifungal activity to each test microbial as compared with those of Examples 15 and 16. Therefore, it is preferable to use zinc acetate, zinc sulfate or zinc chloride as a raw material for synthesizing zinc oxide and/or zinc basic carbonate. And it is preferable that when zinc sulfate or zinc chloride is used as a raw material, it is preferable to add acetic acid to zinc (mole number; acetic acid/zinc=2).

Further, antibacterial and antifungal activity was tested for cosmetic compositions containing powders obtained in Examples 12, 13, 14, 16 and 17.

The result is shown in Table 5.

TABLE 5

| Sample(wt %) | Blending example | | | | |
|---|---|---|---|---|---|
| | 11 | 12 | 13 | 14 | 15 |
| Example 12 | 5 | — | — | — | — |
| Example 13 | — | 5 | — | — | — |
| Example 14 | — | — | 5 | — | — |
| Example 17 | — | — | — | 5 | — |
| Example 16 | — | — | — | — | 5 |
| Mica | 20 | 20 | 20 | 20 | 20 |
| Silica | 63 | 63 | 63 | 63 | 63 |
| Dimethylpolysiloxane | 1 | 1 | 1 | 1 | 1 |
| Diisostearyl malate | 5 | 5 | 5 | 5 | 5 |
| Glyceryl trioctanoate | 5 | 5 | 5 | 5 | 5 |
| Sorbitan sesquioleate | 1 | 1 | 1 | 1 | 1 |
| Stimulating property | ○ | ○ | ○ | ○ | ○ |
| Easiness of spreading | ○ | ○ | ○ | ○ | ○ |

TABLE 5-continued

| Sample(wt %) | Blending example | | | | |
|---|---|---|---|---|---|
| | 11 | 12 | 13 | 14 | 15 |
| Antibacterial and antifungal activity | ○ | ○ | ○ | X | X |

It was apparently seen from Table 5 that cosmetic compositions of Blending examples 11 to 13 have excellent antibacterial and antifungal property as compared with cosmetic compositions of Blending examples 14 and 15. Therefore, it was confirmed also in powder-blended cosmetic compositions that it is preferable to use zinc acetate, zinc sulfate or zinc chloride as a raw material for synthesizing zinc oxide. And when zinc sulfate or zinc chloride is used, it is preferable to add acetic acid to zinc at double mole number.

Zinc acetate is relatively expensive as an industrial material, but it was seen that even when a material different from zinc acetate is used as a raw material for synthesizing zinc oxide, by adding acetic acid at a mole number which is 2-fold a mole number of zinc, a powder having more excellent antibacterial and antifungal activity over that of a powder synthesized using zinc acetate as a synthesis material can be synthesized.

When acetic acid is not used, an alkali metal salt is flown out by washing of a powder, effect is reduced to half.

Content of Zinc Oxide and/or Zinc Basic Carbonate

Subsequently, the influence by content of zinc oxide was studied for PA inhibitory activity, antibacterial and antifungal property and use feeling.

EXAMPLE 18

Ion-exchanged water is placed into a reaction vessel, and 100 g of talc (JA-24R™: manufactured by ASADA SEIFUN CO., LTD., zeta-potential:−17.0 mV) is dispersed therein. To this were connected two microtube pumps, and pH controller and a stirring apparatus were set. Two microtube pumps were connected to each of a solution in which zinc chloride and acetic acid were dissolved in ion-exchanged water, and a solution in which anhydrous sodium carbonate was dissolved in ion-exchanged water, and fixed so that each solution can be added dropwise to the reaction vessel. Each solution changed as Table 6. A reaction was performed by adjusting amounts of two aqueous solutions to be added dropwise, while stirring under atmospheric pressure and room temperature, and kept constantly pH10 during the reaction. An addition dropwise time was about 30 minutes. The resulting precipitates were washed with water, and filtered three times repeatedly, dried in an oven at 105° C. for 12 hours, ground with a personal mill, and fired at 300° C. for 1 hour. This powder was passed through a 100 mesh sieve after grinding, to obtain an objective material having different contents of zinc oxide. These are designated as Examples 18-2 to 18-11 depending on a content of zinc oxide, as described in Table 6.

EXAMPLE 18-1

Talk (JA-24R™: manufactured by ASADA SEIFUN CO., LTD)

TABLE 6

|  | Zinc solution | | | | Alkali solution | |
| --- | --- | --- | --- | --- | --- | --- |
|  | Content of zinc oxide (wt %) | Ion exchanged water (mL) | Zinc chloride (g) | Acetic acid (g) | Ion exchanged water (mL) | Anhydrous sodium carbonate (g) |
| Example 18-2 | 1 | 8 | 1.67 | 1.48 | 13.5 | 4.42 |
| Example 18-3 | 5 | 40 | 8.35 | 7.4 | 67.5 | 22.1 |
| Example 18-4 | 10 | 80 | 16.7 | 14.8 | 135 | 44.2 |
| Example 18-5 | 20 | 160 | 33.4 | 29.6 | 270 | 88.4 |
| Example 18-6 | 30 | 240 | 50.1 | 44.4 | 405 | 132.6 |
| Example 18-7 | 40 | 320 | 66.8 | 59.2 | 540 | 176.8 |
| Example 18-8 | 50 | 400 | 83.5 | 74 | 675 | 221 |
| Example 18-9 | 60 | 480 | 100.2 | 88.8 | 810 | 265.2 |
| Example 18-10 | 75 | 600 | 125.25 | 111 | 1012.5 | 331.5 |
| Example 18-11 | 90 | 720 | 150.3 | 133.2 | 1215 | 397.8 |

PA inhibitory activity, antibacterial and antifungal activity and easiness of spreading of powders obtained in Examples 18-1 to 18-11 were tested by the above method and criteria. The result is shown in Table 7.

TABLE 7

| Example | Content of zinc oxide (%) | PA inhibiting rate (%) | Antibacterial and antifungal activity | | | | | | Easiness of spreading |
| --- | --- | --- | --- | --- | --- | --- | --- | --- | --- |
|  |  |  | (1) | (2) | (3) | (4) | (5) | (6) |  |
| 18-1 | 0 | 20 | E | E | E | E | E | E | ○ |
| 18-2 | 1 | 30 | E | E | D | E | E | E | ○ |
| 18-3 | 5 | 42 | D | D | B | D | E | D | ○ |
| 18-4 | 10 | 47 | C | C | A | D | D | B | ○ |
| 18-5 | 20 | 53 | A | A | A | A | B | A | ○ |
| 18-6 | 30 | 55 | A | A | A | A | A | A | ○ |
| 18-7 | 40 | 54 | A | A | A | A | A | A | ○ |
| 18-8 | 50 | 55 | A | A | A | A | A | A | ○ |
| 18-9 | 60 | 54 | A | A | A | A | A | A | ○ |
| 18-10 | 75 | 53 | A | A | A | A | A | A | ○ |
| 18-11 | 90 | 54 | A | A | A | A | A | A | X |

(1) Blue mold
(2) Black mold
(3) *Candida albicans*
(4) *Pseudomonas aeruginosa*
(5) *Escherichia coli*
(6) *Staphylococcus aureus*

As seen from Table 7, at a content of zinc oxide of 5% by weight or larger, a PA inhibiting rate was increased, and antibacterial and antifungal activity was also improved. However, in Example 18-11 containing zinc oxide at 90% by weight, spreading was difficult, and there is a possibility that usability at blending in a cosmetic composition is deteriorated. From the forgoing results, a content of zinc oxide is preferably 5 to 75% by relative to the whole composite powder.

Further, antibacterial and antifungal activity, stimulating property and easiness of spreading of cosmetic compositions containing powders obtained in Examples 18-2 to 18-11 were tested. Result is shown in Table 8.

TABLE 8

|  | Blending example 16- | | | | | | | | | |
| --- | --- | --- | --- | --- | --- | --- | --- | --- | --- | --- |
| Sample(wt %) | 1 | 2 | 3 | 4 | 5 | 6 | 7 | 8 | 9 | 10 |
| Example 18-2 | 5 | — | — | — | — | — | — | — | — | — |
| Example 18-3 | — | 5 | — | — | — | — | — | — | — | — |
| Example 18-4 | — | — | 5 | — | — | — | — | — | — | — |
| Example 18-5 | — | — | — | 5 | — | — | — | — | — | — |
| Example 18-6 | — | — | — | — | 5 | — | — | — | — | — |
| Example 18-7 | — | — | — | — | — | 5 | — | — | — | — |
| Example 18-8 | — | — | — | — | — | — | 5 | — | — | — |
| Example 18-9 | — | — | — | — | — | — | — | 5 | — | — |
| Example 18-10 | — | — | — | — | — | — | — | — | 5 | — |
| Example 18-11 | — | — | — | — | — | — | — | — | — | 5 |
| Talc | 20 | 20 | 20 | 20 | 20 | 20 | 20 | 20 | 20 | 20 |
| Mica | 63 | 63 | 63 | 63 | 63 | 63 | 63 | 63 | 63 | 63 |
| Dimethylpolysiloxane | 1 | 1 | 1 | 1 | 1 | 1 | 1 | 1 | 1 | 1 |
| Diisostearyl malate | 5 | 5 | 5 | 5 | 5 | 5 | 5 | 5 | 5 | 5 |
| Glyceryl trioctanoate | 5 | 5 | 5 | 5 | 5 | 5 | 5 | 5 | 5 | 5 |
| Sorbitan sesquioleate | 1 | 1 | 1 | 1 | 1 | 1 | 1 | 1 | 1 | 1 |
| Antibacterial and antifungal activity | Δ | ○ | ○ | ○ | ○ | ○ | ○ | ○ | ○ | ○ |
| Stimulating property | ○ | ○ | ○ | ○ | ○ | ○ | ○ | ○ | ○ | ○ |
| Easiness of spreading | ○ | ○ | ○ | ○ | ○ | ○ | ○ | ○ | Δ | X |

As seen from Table 8, cosmetic compositions containing composite powders in Examples 18-2 to 11 having a content of 5% by weight of zinc oxide or larger showed high antibacterial and antifungal activity. However, in a cosmetic composition containing the composite powder in Example 18-11 containing 90% by weight of zinc oxide, spreading was difficult. From the forgoing results, it was also confirmed in powder-blended cosmetic composition that a content of zinc oxide is preferably 5 to 75% by weight relative to the whole composite powder.

Content of Alkali Metal Salt

Subsequently, what differences are produced in PA inhibitory activity and antibacterial and antifungal activity by an amount of an alkali metal salt was studied.

EXAMPLE 19

Ion-exchanged water is placed into a reaction vessel, and 100 g of talc (JA-68R™: manufactured by ASADA SEIFUN CO., LTD., zeta-potential:−19.3 mV) is dispersed therein. To this were connected two microtube pumps, and pH controller and a stirring apparatus were set. Two microtube pumps were connected to each of a solution in which 33.4 g of zinc chloride and 29.6 g of acetic acid were dissolved in 160 mL of ion-exchanged water, and a solution in which 36 g of sodium hydroxide was dissolved in 400 mL of ion-exchanged water, and fixed, so that each solution can be added dropwise to the reaction vessel. A reaction was performed by adjusting amounts of two aqueous solutions to be added dropwise, while stirring under atmospheric pressure and room temperature, and kept constantly pH 8 during the reaction. An addition dropwise time was about 30 minutes. The resulting precipitates were washed with water, and filtered three times repeatedly, dried in an oven at 105° C. for 12 hours, ground with a personal mill, and fired at 300° C. for 1 hour. This powder was passed through a 60 mesh sieve after grinding, to obtain an objective preliminary powder (composite powder of talc and zinc oxide).

The aforementioned preliminary powder was added to an aqueous solution in which sodium carbonate was dissolved in 20 mL of ion-exchanged water, the materials were sufficiently stirred and mixed with a homomixer, and dried using an oven at 110° C. for 14 hours to obtain an objective material. A mixing amount of sodium carbonate and a preliminary powder was changed as shown in Table 9, to obtain composite powders having different contents of an alkali metal salt.

TABLE 9

|  | Mixed quantity (g) | | Sodium carbonate |
| --- | --- | --- | --- |
|  | Preliminary powder | Sodium carbon | content (wt %) |
| Example 19-1 | 10 | 0 | 0 |
| Example 19-2 | 9.975 | 0.025 | 0.25 |
| Example 19-3 | 9.95 | 0.05 | 0.50 |
| Example 19-4 | 9.9 | 0.1 | 1.00 |
| Example 19-5 | 9.75 | 0.25 | 2.50 |
| Example 19-6 | 9.5 | 0.5 | 5.00 |
| Example 19-7 | 9 | 1 | 10.00 |
| Example 19-8 | 7.5 | 2.5 | 25.00 |
| Example 19-9 | 5 | 5 | 50.00 |
| Example 19-10 | 2.5 | 7.5 | 75.00 |
| Example 19-11 | 0 | 10 | 100.00 |

PA inhibitory activity and antibacterial and antifungal activity of powders obtained in Examples 19-1 to 19-11 were tested by the above method and criteria. The result is shown in Table 10.

TABLE 10

| Example | Content of sodium carbonate (%) | PA inhibiting rate (%) | Antibacterial and antifungal activity | | | | | |
| --- | --- | --- | --- | --- | --- | --- | --- | --- |
|  |  |  | (1) | (2) | (3) | (4) | (5) | (6) |
| 19-1 | 0 | 52 | E | E | D | E | D | D |
| 19-2 | 0.25 | 53 | E | D | D | E | D | D |
| 19-3 | 0.5 | 52 | D | D | B | D | C | D |
| 19-4 | 1 | 51 | C | C | B | D | C | C |
| 19-5 | 2.5 | 53 | A | A | A | C | B | B |
| 19-6 | 5 | 52 | A | A | A | A | B | A |
| 19-7 | 10 | 53 | A | A | A | A | A | A |
| 19-8 | 25 | 51 | A | A | A | A | A | A |
| 19-9 | 50 | 35 | A | A | A | A | B | A |
| 19-10 | 75 | 15 | A | A | A | A | B | A |
| 19-11 | 100 | 10 | D | B | A | A | B | A |

(1) Blue mold
(2) Black mold
(3) *Candida albicans*
(4) *Pseudomonas aeruginosa*
(5) *Escherichia coli*
(6) *Staphylococcus aureus*

As apparent from Table 10, at a content of sodium carbonate of 50% by weight or larger, as a content of sodium carbonate was increased, a PA inhibiting rate was decreased.

Little antibacterial and antifungal activity was seen in Example 19-1 composed of only a preliminary powder and, at a content of sodium carbonate of 0.5% by weight or larger, as the content was increased, the activity was improved. However, at a content of sodium carbonate of 75% by weight or larger, deterioration in activity of a composition due to high hygroscopicity and dissolution out property of sodium carbonate, and influence of an antibacterial agent itself on a human body due to strong alkali property are feared. Further, in Example 19-11 containing 100% by weight of sodium carbonate, the effect on blue mold and black mold was decreased.

From this result, it was confirmed that a content of an alkali metal salt is preferably 0.5 to 50% by weight of the whole composite powder.

Based on this result, when a preliminary powder and an alkali metal salt were simply mixed in the powder state, it was found out antibacterial and antifungal activity is improved. However, although better antibacterial property is exhibited at an early stage, it was confirmed that an alkali metal salt easily dissolved out, and the effect does not continue. For this reason, in order that antibacterial and antifungal activity continues over a long term, it is preferable that zinc oxide and an alkali metal salt are sufficiently mixed, and an alkali metal salt is encapsulated in a fine aggregate of zinc oxide.

Further, antibacterial and antifungal activity, stimulating property and easiness of spreading of cosmetic compositions containing powders obtained in Examples 19-1 to 19-11 were tested. The result is shown in Table 11.

TABLE 11

| Sample(wt %) | Blending example 17- | | | | | | | | | | |
|---|---|---|---|---|---|---|---|---|---|---|---|
| | 1 | 2 | 3 | 4 | 5 | 6 | 7 | 8 | 9 | 10 | 11 |
| Example 19-1 | 5 | — | — | — | — | — | — | — | — | — | — |
| Example 19-2 | — | 5 | — | — | — | — | — | — | — | — | — |
| Example 19-3 | — | — | 5 | — | — | — | — | — | — | — | — |
| Example 19-4 | — | — | — | 5 | — | — | — | — | — | — | — |
| Example 19-5 | — | — | — | — | 5 | — | — | — | — | — | — |
| Example 19-6 | — | — | — | — | — | 5 | — | — | — | — | — |
| Example 19-7 | — | — | — | — | — | — | 5 | — | — | — | — |
| Example 19-8 | — | — | — | — | — | — | — | 5 | — | — | — |
| Example 19-9 | — | — | — | — | — | — | — | — | 5 | — | — |
| Example 19-10 | — | — | — | — | — | — | — | — | — | 5 | — |
| Example 19-11 | — | — | — | — | — | — | — | — | — | — | 5 |
| Talc | 20 | 20 | 20 | 20 | 20 | 20 | 20 | 20 | 20 | 20 | 20 |
| Mica | 63 | 63 | 63 | 63 | 63 | 63 | 63 | 63 | 63 | 63 | 63 |
| Dimethylpoly-siloxane | 1 | 1 | 1 | 1 | 1 | 1 | 1 | 1 | 1 | 1 | 1 |
| Diisostearyl malate | 5 | 5 | 5 | 5 | 5 | 5 | 5 | 5 | 5 | 5 | 5 |
| Glyceryl trioctanoate | 5 | 5 | 5 | 5 | 5 | 5 | 5 | 5 | 5 | 5 | 5 |
| Sorbitan sesquioleate | 1 | 1 | 1 | 1 | 1 | 1 | 1 | 1 | 1 | 1 | 1 |
| Antibacterial and antifungal activity | X | Δ | Δ | ◯ | ◯ | ◯ | ◯ | ◯ | ◯ | ◯ | Δ |
| Stimulating property | ◯ | ◯ | ◯ | ◯ | ◯ | ◯ | ◯ | ◯ | ◯ | Δ | X |
| Easiness of spreading | ◯ | ◯ | ◯ | ◯ | ◯ | ◯ | ◯ | ◯ | ◯ | Δ | Δ |

As apparent from Table 11, little antibacterial and antifungal activity was seen in Example 19-1 containing only a preliminary powder and, at a content of sodium carbonate 0.5% by weight or larger, the effect was exerted. However, in Example 19-10 containing 100% by weight of sodium carbonate, the effect was decreased. In particular, at a content of sodium carbonate of 1 to 75% by weight, the effect was better. In addition, at a content of sodium carbonate of 75% by weight or larger, a possibility that activity of a composition is deteriorated due to high hygroscopicity and dissolution out of sodium carbonate, or an antibacterial agent itself becomes strong alkaline property is feared.

From this result, it was confirmed that a content of an alkali metal salt is preferably 0.5 to 50% by weight of the whole composite powder also in a powder-blended cosmetic composition.

pH at Synthesis and pH of Aqueous Dispersion

Figure 6:
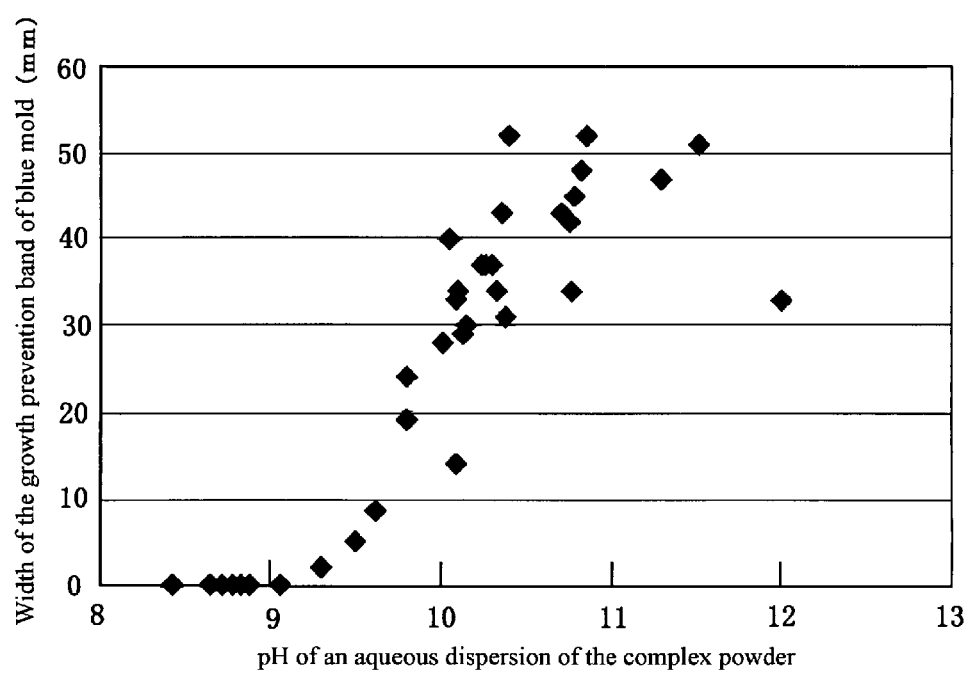
FIG. 6 is a view showing a relationship between pH of an aqueous dispersion of the composite powder of the present invention and moldproofing activity against blue mold.

FIG. 6 shows a relationship between antifungal activity on blue mold, and pH of an aqueous dispersion when a composite powder was dispersed in water into a 10% by weight slurry. Antifungal activity is expressed by a width of a growth inhibition band by the aforementioned method. As shown in the same figure, it is seen that a powder having high moldproofing property has pH of an aqueous dispersion of 9 to 14, particularly 9.5 to 12. Therefore, pH of a 10% by weight aqueous dispersion is preferably 9 to 14, most preferably 9.5 to 12.

In addition, it was found that pH at synthesis is greatly involved in a factor of increasing pH of a dispersion of a powder in water. That is, it was seen that when pH upon synthesis of a composite powder is controlled at 7 to 10, a dispersion of a synthesized powder in water tends to exhibit pH of 9 to 14.

Then, a relationship between pH at synthesis, and PA inhibitory activity and antibacterial and antifungal activity was studied in detail.

EXAMPLE 20

Ion-exchanged water is placed into a reaction vessel, and 100 g of talc (FIT POWDER FK-300S™: manufactured by YAMAGUCHI MICA CO., zeta-potential:−19.3 mV) is dispersed thererin. To this were connected two microtube pumps, and a pH controller and a stirring apparatus were set. Two microtube pumps were connected to each of a solution in which 66.8 g of zinc chloride and 59.2 g of acetic acid were dissolved in 320 mL of ion-exchanged water, and a 33% of anhydrous sodium carbonate aqueous solution, and fixed so that each solution can be added dropwise to the reaction vessel. A reaction was performed by adjusting amounts of two aqueous solutions to be added dropwise, while stirring under atmospheric pressure and room temperature, and kept constantly pH as Table 12 during the reaction. The resulting precipitates were washed with water, and filtered three times repeatedly, dried in an oven at 105° C. for 12 hours, ground with a personal mill, and fired at 300° C. for 1 hour. This powder was passed through a 100 mesh sieve after grinding, to obtain an objective material.

These are designated as Examples 20-1 to 20-5 depending on pH at synthesis, as described in Table 12.

EXAMPLE 20-6

Talk (FIT POWDER FK-300S™)

TABLE 12

| | | Alkali solution | |
|---|---|---|---|
| | pH at synthesis | Ion-exchange water (mL) | Sodium carbonate anhydrous (g) |
| Example 20-1 | 6 | 350 | 115.5 |
| Example 20-2 | 7 | 440 | 145.2 |
| Example 20-3 | 8 | 540 | 176.8 |
| Example 20-4 | 9 | 720 | 235.2 |
| Example 20-5 | 10 | 1020 | 386.8 |

PA inhibitory activity and antibacterial and antifungal activity of powders obtained in Examples 20-1 to 20-6 were tested by the above method and criteria, and the relation with the pH at synthesis were investigated.

The result is shown in Table 13.

TABLE 13

| Example | pH at synthesis | PA inhibiting rate (%) | Antibacterial and antifungal activity | | | | | |
|---|---|---|---|---|---|---|---|---|
| | | | (1) | (2) | (3) | (4) | (5) | (6) |
| 20-1 | 6 | 35 | A | A | A | A | A | A |
| 20-2 | 7 | 43 | A | A | A | A | A | A |
| 20-3 | 8 | 52 | A | A | A | A | A | A |
| 20-4 | 9 | 53 | A | A | A | D | D | B |
| 20-5 | 10 | 54 | C | C | D | D | D | E |
| 20-6 | 11 | 53 | D | D | D | E | E | E |
| 20-7 | — | 25 | E | E | E | E | E | E |

(1) Blue mold
(2) Black mold
(3) *Candida albicans*
(4) *Pseudomonas aeruginosa*
(5) *Escherichia coli*
(6) *Staphylococcus aureus*

From Table 13, PA inhibiting rate was increased when pH at synthesis was 7 to 11, and antibacterial and antifungal activity was excellent when pH at synthesis was 6 to 10. From the forgoing results, pH at synthesis is preferably 7 to 10. This is thought because pH of dispersion of synthesized powder in water tends to exhibit to be 9 to 14 when pH at synthesis is controlled at 7 to 10, PA inhibitory activity and antibacterial and antifungal activity become excellent as described above.

And, it was seen that, in the present invention, all powders exhibiting better PA inhibitory activity and antibacterial and antifungal activity exhibit pH of 9 to 14 when prepared into 10% by weight aqueous dispersion. Therefore, in the present invention, pH of 10% by weight of composite powder in aqueous dispersion is preferably 9 to 14.

Studies were further performed in detail for antibacterial and antifungal activity, stimulating property and spreading property of cosmetic compositions of the present invention.

The result is shown in Table 14.

TABLE 14

| | Blending example | | | | |
|---|---|---|---|---|---|
| Sample(wt %) | 18 | 19 | 20 | 21 | 22 |
| Sodium carbonate-containing-zinc oxide covering talc | 5 | 4 | — | — | — |
| Sodium carbonate-containing-zinc oxide | — | — | — | — | 5 |
| Ethylparaben | — | 0.1 | 0.1 | 0.5 | — |
| Talc | 21 | 21.9 | 25.9 | 25.5 | 21 |
| Mica | 62 | 62 | 62 | 62 | 62 |
| Dimethylpolysiloxane | 1 | 1 | 1 | 1 | 1 |
| Diisostearyl malate | 5 | 5 | 5 | 5 | 5 |
| Glyceryl trioctanoate | 5 | 5 | 5 | 5 | 5 |
| Sorbitan sesquioleate | 1 | 1 | 1 | 1 | 1 |
| Antibacterial and antifungal activity | ◯ | ◯ | X | ◯ | ◯ |
| Stimulating property | ◯ | Δ | Δ | X | ◯ |
| Easiness of spreading | ◯ | ◯ | ◯ | ◯ | Δ |

As apparent from Table 14, Blending example 20 containing 0.1% by weight of ethylparaben showed easy spreading property but no antibacterial and antifungal activity. In order to obtain antibacterial and antifungal activity, it was necessary to blend ethylparaben at 0.5% by weight as seen in Blending example 21. However, in the case of Blending example 18 containing 5% by weight of the composite powder of the present invention, sufficient antibacterial and antifungal activity was exhibited without ethylparaben. Further, spreading was easy, and usability was better. In addition, in Blending example 19 containing 4% by weight of the composite powder of the present invention, even when an amount of ethylparaben is reduced to 0.1% by weight, better easy spreading and antibacterial and antifungal activity are possessed. In addition, in Blending example 22 using sodium carbonate-containing zinc oxide, which is not combined with a base powder, inferior easiness of spreading was observed.

Since the composite powder of the present invention does not use an expensive raw material such as silver- and zinc-substituted zeolite, it is inexpensive as compared with the conventional inorganic antibacterial agent. The composite powder of the present invention has advantage in problems which were frequently observed in the conventional antibacterial agent. That is, time-dependent changes such as discoloration and color degradation of antibacterial agent itself or composition containing the antibacterial agent are little. Further, to state specially, the composite powder of the present invention exhibits high effect also on fungi such as mold and yeast against which the conventional inorganic antibacterial and antifungal agent had low effect.

| Embodiment 1 Cream | | |
|---|---|---|
| | (prescription) | wt % |
| 1) | Stearic acid monoglyceride | 2.0 |
| 2) | Stearyl alcohol | 4.0 |
| 3) | Bee wax | 3.0 |
| 4) | Lanolin | 5.0 |
| 5) | P.O.E (20 mol) sorbitan monooleate | 2.0 |
| 6) | Squalane | 20.0 |
| 7) | Sodium carbonate-containing-zinc oxide covering talc | 5.0 |
| 8) | perfume | 0.2 |
| 9) | 1,3-Butylene glycol | 5.0 |
| 10) | Glycerol | 5.0 |
| 11) | Purified water | remainder |
| (process) | | |

1) to 6) and 8) are heated and kept at 75° C. (oily phase). 9) and 10) are dissolved in 11), added and dispersed 7) and heated to 75° C. (aqueous phase). The aqueous phase is added to the oily phase and emulsified homogeneously with a homomixer, and cooled down to 30° C. with sufficient stirring.

| Embodiment 2 Baby powder | | |
|---|---|---|
| | (prescription) | wt % |
| 1) | Talc | 80.4 |
| 2) | Calcium carbonate | 17.0 |
| 3) | Starch | 0.5 |
| 4) | Sodium carbonate-containing-zinc oxide silica complex | 2.0 |
| 5) | Antiseptics | 0.1 |
| (process) | | |

1) to 5) are stirred to mix well with a blender.

| | Embodiment 3 Emulsifying foundation | |
|---|---|---|
| | (prescription) | wt % |
| 1) | Stearic acid | 0.4 |
| 2) | Isostearic acid | 0.3 |
| 3) | Cetyl 2-ethylhexanoate | 4.0 |
| 4) | Liquid paraffin | 11.0 |
| 5) | P.O.E (10) stearyl ether | 2.0 |
| 6) | Talc | 15.0 |
| 7) | Red iron oxide | 0.01 |
| 8) | Yellow iron oxide | 0.001 |
| 9) | Black iron oxide | 0.05 |
| 10) | Cetyl alcohol | 0.3 |
| 11) | Lithium hydroxide-containing-zinc oxide covering silica | 5.0 |
| 12) | Triethanolamine | 0.4 |
| 13) | Dipropylene glycol | 5.0 |
| 14) | Perfume | 0.01 |
| 15) | Purified water (process) | remainder |

After 1) to 10) are heated to 85° C. to dissolve them, 11) is added and uniformly dispersed. Into this, a mixture of 12), 13) and 15) which had been heated to 85° C. to dissolve them, gradually added to emulsify. The emulsion is stirred keeping the emulsification temperature for 10 minutes, and cooled to 45° C. while stirring. To this, 14) is added, the mixture is continuously cooled to 35° C. while stirring, and this is charged into a container.

| | Embodiment 4 Pack | |
|---|---|---|
| | (prescription) | wt % |
| 1) | Polyvinyl alcohol | 15.0 |
| 2) | Polyethylene glycol | 3.0 |
| 3) | Propylene glycol | 7.0 |
| 4) | Ethanol | 10.0 |
| 5) | Sodium carbonate-containing-zinc oxide covering silica | 10.0 |
| 6) | Perfume | 0.1 |
| 7) | Purified water (process) | remainder |

2) and 3) are added to 7) to dissolve them. Next 1) is added, heated and dissolved, and 5) is dispersed. Added 4) and 6) to dissolved them while stirring.

| | Embodiment 5 Solid powder foundation | |
|---|---|---|
| | (prescription) | wt % |
| 1) | Sericite | 22.0 |
| 2) | Synthesis mica | 15.0 |
| 3) | Talc | remainder |
| 4) | Sodium carbonate-containing-zinc oxide covering silica | 7.0 |
| 5) | Ferric oxide | 0.8 |
| 6) | Yellow iron oxide | 2.0 |
| 7) | Black iron oxide | 0.1 |
| 8) | Zinc white | 2.0 |
| 9) | Silicone elastic powder | 2.0 |
| 10) | Spherical polyethylene | 4.0 |
| 11) | Dimethylpolysiloxane | 3.0 |
| 12) | Liquid paraffin | 5.0 |
| 13) | Vaseline | 5.0 |
| 14) | Sorbitan sesquiisostearate | 1.0 |

| | Embodiment 5 Solid powder foundation | |
|---|---|---|
| | (prescription) | wt % |
| 15) | Anti-oxidant | proper quantity |
| 16) | Perfume (process) | proper quantity |

1) to 16) are stirred to mix well with a blender.

| | Embodiment 6 W/O type emulsified makeup foundation | |
|---|---|---|
| | (prescription) | wt % |
| 1) | Cyclomethicone | 30.0 |
| 2) | Dimethicone | 2.0 |
| 3) | Silicone resin | 1.0 |
| 4) | Antioxidant | proper quantity |
| 5) | Octyl methoxy cinnamate | 3.0 |
| 6) | 4-tert butyl-4'-methoxy benzoylmethane | 1.0 |
| 7) | Isostearic acid | 1.0 |
| 8) | Silicone treated alumina | 8.0 |
| 9) | Cation modified bentonite | 2.0 |
| 10) | Sodium carbonate-containing-zinc oxide covering talc | 5.0 |
| 11) | Talc | 5.0 |
| 12) | Spherical PMMA resin powder | 5.0 |
| 13) | Purified water | remainder |
| 14) | Glycerol | 4.0 |
| 15) | 1,3-Propylene glycol | 1.0 |
| 16) | Stabilizer | proper quantity |
| 17) | Perfume (process) | proper quantity |

1) to 9), 12), 16) and 17) are heated to 85° C. to dissolve them, and 10) and 11) are added and dispersed (oily phase). 14) and 15) are added to 13), and are uniformly dispersed (aqueous phase). An oily phase is added to an aqueous phase, this is stirred while retaining at 85° C. for 100 minutes, and cooled to 45° C. while stirring.

| | Embodiment 7 W/O style emulsifying foundation | |
|---|---|---|
| | (prescription) | wt % |
| 1) | Silicone treated synthesis mica | 15.0 |
| 2) | Silicone treated sericite | 7.0 |
| 3) | Silicone treated titanium oxide | 12.0 |
| 4) | Silicone treated ferric oxide | 1.2 |
| 5) | Silicone treated yellow iron oxide | 2.3 |
| 6) | Silicone treated black iron oxide | 0.6 |
| 7) | Potassium hydrogencarbonate-containing-zinc oxide covering mica | 12.0 |
| 8) | Spherical PMMA powder | 4.0 |
| 9) | Cyclomethicone | remainder |
| 10) | Dimethylpolysiloxane | 4.0 |
| 11) | Squalane | 3.0 |
| 12) | Polyether modifed silicone | 2.0 |
| 13) | Sorbitan sesqui isostearate | 1.0 |
| 14) | Dispersant | Proper quantity |
| 15) | Dipropylene glycol | 2.0 |
| 16) | Phenoxyethanol | 0.1 |
| 17) | Purified water | 20.0 |
| 18) | Antioxidant | proper quantity |
| 19) | Perfume (process) | proper quantity |

1) to 14) are heated to 85° C. to dissolve them (oily phase). 16) is added to 17), and are uniformly dispersed (aqueous phase). An oily phase is added to an aqueous phase, this is stirred while retaining at 85° C. for 100 minutes, added 18) and 19), and cooled to 45° C. while stirring.

Embodiment 8 White powder

| | (prescription) | wt % |
|---|---|---|
| 1) | Talc | remainder |
| 2) | Synthesis mica | 22.0 |
| 3) | Sodium hydroxide-containing-zinc oxide covering talc | 13.0 |
| 4) | Spherical silicone powder | 4.0 |
| 5) | Squalane | 3.0 |
| 6) | Perfume (process) | proper quantity |

1) to 5) are stirred to mix well with a blender, and 6) is sprayed uniformly.

Embodiment 9 O/W type emulsifying foundation

| | (prescription) | wt % |
|---|---|---|
| 1) | Sericite | 17.0 |
| 2) | Mica | 20.0 |
| 3) | Lithium carbonate-containing-zinc oxide covering mica | 8.0 |
| 4) | Ferric oxide | 0.3 |
| 5) | Yellow iron oxide | 1.2 |
| 6) | Black iron oxide | 0.6 |
| 7) | Spherical polyethylene powder | 6.0 |
| 8) | Squalane | 10.0 |
| 9) | Olive oil | 10.0 |
| 10) | Stearic acid | 2.0 |
| 11) | Glyceryl monostearate | 2.0 |
| 12) | Sorbitan POE (40) monostearate | 2.0 |
| 13) | Glycerol | 5.0 |
| 14) | Hexane 1,2-diol | 1.0 |
| 15) | Triethanolamine | 0.8 |
| 16) | pH modifier | proper quantity |
| 17) | Purified water (process) | remainder |

1) to 12) are heated to 85° C. to dissolve them (oily phase). 13) to 16) are added to 17), and are uniformly dispersed (aqueous phase). An oily phase is added to an aqueous phase, this is stirred while retaining at 85° C. for 100 minutes and cooled to 45° C. while stirring.

Embodiment 10 O/W type emulsifying makeup foundation

| | (prescription) | wt % |
|---|---|---|
| 1) | Purified water | remainder |
| 2) | Glycerol | 20.0 |
| 3) | Pentane 1,2-diol | 3.0 |
| 4) | 1,3-Butylene glycol | 1.0 |
| 5) | Liquid paraffin | 7.5 |
| 6) | Isostearic acid | 0.5 |
| 7) | Ascorbic acid (whitening agent) | 0.2 |
| 8) | Matricaria extract (whitening agent) | 0.1 |
| 9) | Saxifrage extract (whitening agent) | 0.3 |
| 10) | di 2-Ethylhexyl phthalate | 0.3 |
| 11) | Spherical silica | 4.0 |
| 12) | Sodium carbonate-containing-zinc oxide covering talc | 5.0 |
| 13) | Talc | 5.0 |
| 14) | Stabilization agent | proper quantity |
| 15) | Perfume (process) | proper quantity |

5) to 14) are heated to 85° C. to dissolve them (oily phase). 2) to 4) are added to 1), and are uniformly dispersed and heated to 85° C. (aqueous phase). An oily phase is added to an aqueous phase, this is stirred while retaining at 85° C., added 15) and cooled to 45° C. while stirring.

Embodiment 11 Two-way powder foundation

| | (prescription) | wt % |
|---|---|---|
| 1) | Silicone treated sericite | 13.0 |
| 2) | Silicone treated mica | remainder |
| 3) | Silicone treated talc | 15.0 |
| 4) | Potassium carbonate-containing-zinc oxide covering mica | 5.0 |
| 5) | Aluminum stearate treated fine particle titanium oxide | 6.0 |
| 6) | Silicone treated titanium oxide | 9.0 |
| 7) | Silicone treated ferric oxide | 1.2 |
| 8) | Silicone treated yellow iron oxide | 2.5 |
| 9) | Silicone treated black iron oxide | 0.9 |
| 10) | Barium sulfate powder | 7.0 |
| 11) | Polyurethane powder | 1.0 |
| 12) | Silicone elastic powder | 5.0 |
| 13) | Polyethylene powder | 2.0 |
| 14) | Interference titanated mica | 4.0 |
| 15) | Dimethylpolysiloxane | 3.0 |
| 16) | Methyl phenyl polysiloxane | 2.0 |
| 17) | Vaseline | 2.0 |
| 18) | Octyl methoxy cinnamate | 3.0 |
| 19) | Sorbitan sesuqui isostearate | 1.0 |
| 20) | Polyether silicone | 1.0 |
| 21) | Antioxidant | proper quantity |
| 22) | Perfume (process) | proper quantity |

1) to 21) are heated 85° C. while stirring, and then 22) is sprayed uniformly.

Embodiment 12 Two-way powder foundation

| | (prescription) | wt % |
|---|---|---|
| 1) | Fluorine modified silicone treated sericite | 22.0 |
| 2) | Fluorine modified silicone treated mica | remainder |
| 3) | Fluorine modified silicone treated kaolin | 10.0 |
| 4) | Potassium hydrogencarbonate containing zinc oxide covering silica | 7.0 |
| 5) | Silicone treated fine particle titanium oxide | 8.0 |
| 6) | Fluorine modified silicone treated titanium oxide | 9.0 |
| 7) | Fluorine modified silicone treated ferric oxide | 1.2 |
| 8) | Fluorine modified silicone treated yellow iron oxide | 2.5 |
| 9) | Fluorine modified silicone treated black iron oxide | 0.9 |
| 10) | Spherical silicone powder | 8.0 |
| 11) | Lauroyl lysine covering titanium oxide | 4.0 |
| 12) | Dimethylpolysiloxane | 4.0 |
| 13) | Polyethylene glycol | 2.0 |
| 14) | Fluoro polyether | 2.0 |
| 15) | Octyl methoxycinnamate | 2.0 |
| 16) | Sorbitan sesuqui isostearate | 1.0 |
| 17) | Antioxidant | proper quantity |

-continued

Embodiment 12 Two-way powder foundation

| (prescription) | | wt % |
|---|---|---|
| 18) | Perfume | proper quantity |
| | (process) | |

1) to 17) are heated 85° C. while stirring, and then 18) is sprayed uniformly.

Embodiment 13 Wipe substance for cleaning

| | (prescription) | wt % |
|---|---|---|
| 1) | Purified water | 91.945 |
| 2) | Salt (Japanese pharmacopoeia) | 0.35 |
| 3) | Dipropylene glycol | 2.0 |
| 4) | Sodium hexa metaphosphate | 0.005 |
| 5) | Sodium hydrogencarbonate-containing-zinc oxide covering talc | 5.0 |
| 6) | Bentonite | 0.5 |
| 7) | POE (20) octyl dodecyl ether | 0.1 |
| | (process) | |

2) to 7) are dissolved and dispersed in 1) while well stirring, and soaked into nonwoven fabric.

Embodiment 14 Paper powder

| | (prescription) | wt % |
|---|---|---|
| 1) | Colorant | 25 |
| 2) | Sodium carbonate-containing-zinc oxide covering silica | 3 |
| 3) | Carboxymethylcellulose sodium | 0.2 |
| 4) | Sodium metaphosphate | 0.2 |
| 5) | Polyoxyethylene sorbitan monooleate (20E. O.) | 0.2 |
| 6) | Perfume | 0.1 |
| 7) | Common water | proper quantity |
| | Total | 100 wt % |
| | (process) | |

The coating solution that mixed 1) to 6) in 7) are coated on the paper, and dried.

The cosmetic compositions of Embodiments 1 to 14 have excellent antibacterial and antifungal activity and have no stimulating property.

Embodiment 15

Adhesion to Leather, Timber or the Like

The composite powder of the present invention was printed with a binder made of a synthetic resin, and followed by heat treatment to adhere the composite powder by the resin. By these procedures, antibacterial and antifungal effect, and skin roughening inhibiting and improving effect are exerted.

Embodiment 16

Coating on Glass, Metal or the Like

By adding the composite powder of the present invention to an adhesive, and coating this, antibacterial and antifungal effect, and skin roughening inhibiting and improving effect are exerted.

An outline of the process is as follows:
1. A slurry of the composite powder of the present invention is prepared.
2. An adhesive (oxidized starch, resin, resin emulsion etc.) is added.
3. This is uniformly coated, and dried.

Embodiment 17

Filling into Paper, Fiber or the Like

A paper is an extremely rough porous sheet, which is originally made from a main raw material of a plant fiber. When the composite powder of the present invention is filled therein, the powder is retained in the interior. Then antibacterial and antifungal effect, and skin roughening inhibiting and improving effect are exerted.

An outline of the process is as follows.
1. A pulp is dispersed in water, and fibers are cut with a beater to convert into viscous.
2. The composite powder of the present invention is added as filler.
3. This is subjected to a paper making machine.

Embodiment 18

Blending into Garment Detergent or Softness Finishing Agent, or the Like

By blending the composite powder of the present invention into a garment detergent or a softness finishing agent, the composite powder is adhered to a garment to be contacted with a skin, and retained therein. Then antibacterial and antifungal effect, and skin roughening inhibiting and improving effect are exerted.

Embodiment 19

Blending into Powder Product

In powder products such as body powder and powder spray, it was difficult to be blended liquid component such as water and oil. By blending the composite powder of the present invention into such powder product, antibacterial and antifungal effect and skin roughening inhibiting and improving effect, which could not be expected previously, are exerted.

Embodiment 20

Blending into Paste, Varnish, Lacquer, Paint or the Like

By mixing the composite powder of the present invention into a material such as paste, varnish, lacquer and paint, antibacterial and antifungal effect, and skin roughening inhibiting and improving effect are exerted not only in materials itself, but also in materials coated or adhered by said powder.

As explained above, according to the composite powder and the cosmetic composition of the present invention, excellent antibacterial and antifungal property can be obtained by inclusion of zinc oxide and/or zinc basic carbonate, and alkali metal salt.

Further, a composite powder having plasminogen activator inhibitory activity in addition to antibacterial and antifungal effect can be obtained by combining an acting site comprising zinc oxide and/or zinc basic carbonate and an alkali metal salt with an adsorbing site.

What is claimed is:

1. A composite powder having antibacterial and antifungal effect comprising:
    a base powder; wherein said base powder provides an adsorbing site for adsorbing a specified enzyme;
    a zinc oxide and/or zinc basic carbonate; and
    an alkali metal salt;
    wherein said zinc oxide and/or zinc basic carbonate and said alkali metal salt are combined as an acting site to inhibit an activity of said enzyme which is adsorbed by said adsorbing site of said base powder;
    wherein said base powder, said zinc oxide and/or zinc basic carbonate, and said alkali metal salt are combined; and wherein said alkali metal salt is encapsulated in said zinc oxide and/or the zinc basic carbonate,
    wherein said base powder is at least one selected from the group consisting of silica, talc, mica, polyamide, polymethyl methacrylate and silicone resin; and
    wherein said alkali metal salt is at least one selected from the group consisting of lithium hydroxide, sodium hydroxide, potassium hydroxide, lithium hydrogen carbonate, sodium hydrogen carbonate, potassium hydrogen carbonate, lithium carbonate, sodium carbonate and potassium carbonate.

2. The composite powder according to claim 1, wherein a surface of said base powder is covered with said zinc oxide and/or zinc basic carbonate and said alkali metal salt.

3. The composite powder according to claim 2, wherein said surface of said base powder is covered with said zinc oxide and/or zinc basic carbonate and said alkali metal salt in a stripe or spot state or in a net state.

4. The composite powder according to claim 1, wherein said zinc oxide and/or zinc basic carbonate and said alkali metal salt are encapsulated, embedded or included in said base powder.

5. The composite powder according to claim 1, wherein the acting site and the adsorbing site are formed on an inactive powder in a stripe or spot state.

6. The composite powder according to claim 1, wherein said specified enzyme is a plasminogen activator, and said acting site has an inhibitory effect on said plasminogen activator.

7. The composite powder according to claim 1, wherein said adsorbing site of said base powder has a zeta potential at a negative value at a skin pH when said specified enzyme is a plasminogen activator.

8. The composite powder according to claim 1, wherein said adsorbing site of said base powder has a zeta potential at −10 mV or lower at pH 7.5 when said specified enzyme is a plasminogen activator.

9. The composite powder according to claim 1, wherein said alkali metal salt is at 0.5 to 50% by weight of the composite powder.

10. The composite powder according to claim 1, wherein said zinc oxide and/or zinc basic carbonate is at 5 to 75% by weight of the composite powder.

11. The composite powder according to claim 1, wherein said zinc oxide and/or zinc basic carbonate is synthesized by zinc acetate, zinc chloride or zinc sulfate with the presence of acetic acid.

12. The composite powder according to claim 6, wherein said acting site has an inhibitory rate of 40% or more on plasminogen activator when said plasminogen activator is absorbed by said absorbing site on said base powder of the composite powder.

13. The composite powder according to claim 1, wherein a 10% by weight of the composite powder has a pH 9 to 14 when dispersed in water to exert antibacterial and antifungal activity.

14. A cosmetic composition comprising the composite powder according to claim 1.

15. The cosmetic composition according to claim 14, wherein said cosmetic composition does not contain other antibacterial and antifungal agent.

16. The composite powder according to claim 1, wherein said base powder is silica and said alkali metal salt is sodium carbonate.

17. A method for preparing the composite powder of claim 1, comprising:
    supplying an aqueous solution containing said zinc oxide and/or zinc basic carbonate and an aqueous alkali solution containing said alkali metal salt to a reactor containing a base powder to form a reaction solution;
    adjusting said reaction solution with said aqueous solution containing said zinc oxide and/or zinc basic carbonate and said zinc ion and said aqueous alkali solution containing said alkali metal salt to adjust a pH to between 7 to 10 under room temperature and an atmospheric pressure to form a pH adjusted composite powder solution;
    filtering said pH adjusted composite powder solution to form a filtered composite powder; and
    washing said filtered composite powder with water followed by drying to form said composite powder.

* * * * *